United States Patent [19]
Cantor et al.

[11] Patent Number: 5,795,714
[45] Date of Patent: Aug. 18, 1998

[54] METHOD FOR REPLICATING AN ARRAY OF NUCLEIC ACID PROBES

[75] Inventors: Charles R. Cantor; Marek Przetakiewicz; Cassandra L. Smith; Takeshi Sano, all of Boston, Mass.

[73] Assignee: Trustees of Boston University, Boston, Mass.

[21] Appl. No.: 110,691

[22] Filed: Aug. 23, 1993

Related U.S. Application Data

[63] Continuation-in-part of Ser. No. 972,012, Nov. 6, 1992, Pat. No. 5,503,980.

[51] Int. Cl.$^6$ .................................................. C12Q 1/68
[52] U.S. Cl. ............................................. 435/6; 435/6
[58] Field of Search ................. 435/6, 91.1; 536/24.3, 536/24.33, 25.3

[56] References Cited

U.S. PATENT DOCUMENTS

| | | | |
|---|---|---|---|
| 4,808,520 | 2/1989 | Dattagupta et al. | |
| 5,002,867 | 3/1991 | Macevicz | 435/6 |
| 5,068,176 | 11/1991 | Vijg et al. | 435/6 |
| 5,073,483 | 12/1991 | Lebacq | 435/6 |
| 5,106,727 | 4/1992 | Hartley et al. | 435/6 |
| 5,112,734 | 5/1992 | Kramer et al. | 435/6 |
| 5,112,736 | 5/1992 | Caldwell et al. | 435/6 |
| 5,114,839 | 5/1992 | Blocker | 435/6 |
| 5,137,806 | 8/1992 | LaMaistre et al. | |
| 5,149,625 | 9/1992 | Church et al. | 435/6 |
| 5,202,231 | 4/1993 | Drmanac et al. | 435/6 |
| 5,219,726 | 6/1993 | Evans | 435/6 |

FOREIGN PATENT DOCUMENTS

| | | |
|---|---|---|
| 0392546 | 12/1990 | European Pat. Off. |
| WO89 10977 | 11/1989 | WIPO |

OTHER PUBLICATIONS

Hames, "Nucleic acid hybridisation" (1985), pp. 17–45.
Matthews, et al., "Analytical Strategies for the Use of DNA Probes", (1988) Anal. Biochem 169, pp. 1–25.
STRATAGENE Catalog, "Synthetic Oligonucleotides" (1992), p. 106.
Article, "Optical Properties of Specific Complexes Between Complementary Oligoribonucleotides", Robert B. Gennis et al, *Biochemistry*, vol. 9, No. 24, 1970.
Article, "DNA Sequencing By Hybridization: 100 Bases Read By a Non–gel–based Method", Zaklina Strezoska, *Proc. Natl. Acad. Sci. USA*, vol. 88, pp. 10089–10093, Nov. 1991.
Article, "Improved Chips for Sequencing by Hybridization", P.A. Pevzner, et al., *Journal of Biomolecular Structure & Dynamics*, vol. 9, Issue No. 2, 1991.
Article, "A Method for DNA Sequencing By Hybridization with Oligonucleotide Matrix", K.R. Khrapko et al, *DNA Sequence –J. DNA Sequencing and Mapping*, vol. 1, pp. 375–388, 1991.
Article, "Sequence–Selective Recognition of DNA by Strand Displacement with a Thymine–Substituted Polyamide", Peter E. Neilsen et al, *Science*, vol. 254, Dec. 1991.
Article, Parallel Analysis of Oligodeoxyribonucleotide (oligonucleotide) interactions. I. Analysis of Factors Influencing Oligonucleotide Duplex Formation, Uwe Maskos et al, *Nucleic Acids Research*, vol. 20, No. 7, pp. 1675–1678, 1992.

(List continued on next page.)

*Primary Examiner*—Scott W. Houtteman
*Attorney, Agent, or Firm*—James Remenick; Baker & Botts, L.L.P.

[57] ABSTRACT

The invention relates to the replication of probe arrays and methods for replicating arrays of probes which are useful for the large scale manufacture of diagnostic aids used to screen biological samples for specific target sequences. Arrays created using PCR technology may comprise probes with 5'- and/or 3'-overhangs.

29 Claims, 13 Drawing Sheets

OTHER PUBLICATIONS

Article, Oligonucleotide Hybridisations of Glass Supports: A Novel Linker for Oligonucleotide Synthesis and Hybridisation Properties of Oligonucleotides Synthesised in Situ, Uwe Maskos, *Nucleic Acids Research*, vol. 20, No. 7, pp. 1679–1684, 1992.

Article, "Encoded Combinatorial Chemistry", Sydney Brenner, *Proc. Natl. Acad. Sci. USA*, vol. 89, pp. 5381–5383, Jun. 1992.

Article, "Report on the Sequencing by Hybridization Workshop", C.R. Cantor, *Genomics* 13, 1378–1383, 1992.

1–Tuple DNA Sequencing: Computer Analysis, Pavel A. Pevzner et al, *Journal of Biomolecular Structure & Dynamics*, vol. 7, No. 1 (1989), pp. 63–69.

Reliable Hybridization of Oligonucleotides as Short as Six Nucleotides, R. Drmanac et al, *DNA and Cell Boilogy*, vol. 9, No. 7, 1990 pp. 527–534.

"Analytical Strategies for the Use of DNA Probes", Jayne A. Matthews, *Biochemistry*, vol. 169, (1988), pp. 1–25.

"Rapid Detection and Sequencing of Specific in vitro Amplified DNA Sequences Using Solid Phase Methods", Johan Wahlberg et al, *Mol. Cell, Probes*, vol. 4(4), 1990, pp. 285–297.

A New Method for Determining the DNA Nucleotide Sequence by Hybridization with Ologonucleotides, Yu P. Lysov et al, *Doklady Akademii Nauk SSSR*, vol. 303, No. 6, Dec. 1988, 1508–1511.

"An Oligonucleotide Hybridization Approach to DNA Sequencing", K.R. Khrapko et al, *FEBS Letters*, vol. 256, No. 1–2, Oct. 1989, pp. 118–122.

An Algorithm for the DNA Sequence Generation from k–Tuple Word Contents of the Minimal Number of Random Fragments, D. Drmanac et al, *Journal of Biomolecular Structure & Dynamics*, vol. 8, No. 5, (1991) pp. 1085–1102.

FIG. 1

CALCULATED $T_m$ (°C, AVERAGE BASE COMPOSITION)

| NUCLEIC ACID STRUCTURE | n = 8 | 7 | 6 | 5 |
|---|---|---|---|---|
| — | 38 | 33 | 25 | 15 |
| — ⁻ | 33 | 25 | 15 | 3 |
| ⁻ — | 25 | 15 | 3 | -14 |
| = | 51 | 46 | 40 | 31 |
| = ⁻ | 46 | 40 | 31 | 21 |
| ⁻ = | 40 | 41 | 21 | 11 |

BASIC SCHEME FOR POSITIONAL SBH

ALTERNATE SCHEME

LIGATION OF TARGET DNA WITH PROBE

READING AN EXTRA TARGET BASE BY 3' EXTENSION OF THE PROBE

POSITIONAL INFORMATION FROM RATIO OF INTERNAL LABEL (●) TO EXTENSION LABEL (●). A 5' LABEL COULD ALSO BE USED.

READING AN EXTRA TARGET BASE

```
5'————————— AAGCTA —————————3'
             TCGAT —————————•5'
                  │ pppTp
                  ▼
5'————————— AAGCTA —————————3'
           pTTCGAT —————————•5'
                  │
                  ▼
5'————————— AAGCTA —————————3'
            TTCGAT —————————•5'
```

EXTENSION WILL FAIL WITH pppAp, pppGp, AND pppCp

A. 3' EXTENSION OF THE TARGET WITH A pppNp PRIOR TO PHOSPHATASE TREATMENT

ARRAY WITH ONE DEGENERATE BASE

B. HYBRIDIZATION AND LIGATION

FIG. 9

| CHAIN TERMINATOR: | T | G | A |
|---|---|---|---|
| SEQUENCE | | LABEL INTENSITY | |
| GGAAT | 2A, 2G | — | 2G |
| AAGGT | 2A, 2G | 2A | — |
| GAAGT | 2A, 2G | — | 1G |
| AGGAT | 2A, 2G | 1A | — |
| AGAGT | 2A, 2G | 1A | — |
| GAGAT | 2A, 2G | — | 1G |
| GGGAT | 1A, 3G | — | 3G |
| GGAGT | 1A, 3G | — | 2G |
| GAGGT | 1A, 3G | — | 1G |
| AGGGT | 1A, 3G | 1A | — |
| AAAGT | 3A, 1G | 3A | — |
| AAGAT | 3A, 1G | 2A | — |
| AGAAT | 3A, 1G | 1A | — |
| GAAAT | 3A, 1G | — | 1G |
| GGGGT | 4G | — | 1T, 4G* |
| AAAAT | 4A | 1T, 4* | — |

FOUR COLOR ANALYSIS OF SEQUENCE EXTENSION OF THE 3' END OF THE PROBE. LABEL INTENSITY SHOWN DOES NOT INCLUDE CONTRIBUTION FROM THE 3' TERMINATOR.

* PLUS ADDITIONAL POSSIBLE RESIDUES

EXTENSION OF THE PROBE BY LIGATION OF A BLOCKED PENTANUCLEOTIDE. THE PENTANUCLEOTIDE IS 3'-BLOCKED TO PREVENT POLYMERIZATION.

SEQUENCE LISTING ( 1 ) GENERAL INFORMATION:

( i i i ) NUMBER OF SEQUENCES: 48

( 2 ) INFORMATION FOR SEQ ID NO:1:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO:1:

TCGGTTCCAA GAGCT 15

( 2 ) INFORMATION FOR SEQ ID NO:2:

( i ) SEQUENCE CHARACTERISTICS:
( A ) LENGTH: 18 base pairs
( B ) TYPE: nucleic acid
( C ) STRANDEDNESS: single
( D ) TOPOLOGY: linear ( x i ) SEQUENCE DESCRIPTION: SEQ ID NO:2:

CTGATGCGTC GGATCATC 18

( 2 ) INFORMATION FOR SEQ ID NO:3:

( i ) SEQUENCE CHARACTERISTICS:
( A ) LENGTH: 23 base pairs
( B ) TYPE: nucleic acid
( C ) STRANDEDNESS: single
( D ) TOPOLOGY: linear ( x i ) SEQUENCE DESCRIPTION: SEQ ID NO:3:

GATGATCCGA CGCATCAGAG CTC 23

( 2 ) INFORMATION FOR SEQ ID NO:4:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:4:

GATGATCCGA CGCATCAGAG CTT 23

( 2 ) INFORMATION FOR SEQ ID NO:5:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:5:

GATGATCCGA CGCATCAGAG CTA 23

( 2 ) INFORMATION FOR SEQ ID NO:6:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:6:

GATGATCCGA CGCATCAGAG CCC 23

( 2 ) INFORMATION FOR SEQ ID NO:7:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:7:

GATGATCCGA CGCATCAGAG TTC 23

( 2 ) INFORMATION FOR SEQ ID NO:8:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:8:

GATGATCCGA CGCATCAGAA CTC 23

( 2 ) INFORMATION FOR SEQ ID NO:9:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:9:

GATGATCCGA CGCATCAGAG ATC 23

( 2 ) INFORMATION FOR SEQ ID NO:10:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:10:

GATGATCCGA CGCATCAGAG CTT      23

( 2 ) INFORMATION FOR SEQ ID NO:11:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:11:

GATGATCCGA CGCATCAGAT ATC      23

( 2 ) INFORMATION FOR SEQ ID NO:12:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:12:

GATGATCCGA CGCATCAGAT ATT      23

( 2 ) INFORMATION FOR SEQ ID NO:13:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:13:

GATGATCCGA CGCATCAGAG CTCT      24

( 2 ) INFORMATION FOR SEQ ID NO:14:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:14:

GATGATCCGA CGCATCAGAG TTCT      24

( 2 ) INFORMATION FOR SEQ ID NO:15:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:15:

GTCGACAGTT GACGCTACCA YNNNNRTGGT CTAGAGCTAG C      41

( 2 ) INFORMATION FOR SEQ ID NO:16:

( i ) SEQUENCE CHARACTERISTICS:
    ( A ) LENGTH: 41 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:16:

CTCGAGAGTT GACGCTACCA RNNNNYTGGT CTAGACCCGG G      4 1

( 2 ) INFORMATION FOR SEQ ID NO:17:

( i ) SEQUENCE CHARACTERISTICS:
    ( A ) LENGTH: 12 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:17:

GCTAGCTCTA GA      1 2

( 2 ) INFORMATION FOR SEQ ID NO:18:

( i ) SEQUENCE CHARACTERISTICS:
    ( A ) LENGTH: 41 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:18:

GCTAGCTCTA GACCAYNNNN RTGGTAGCGT CAACTGTCGA C      4 1

( 2 ) INFORMATION FOR SEQ ID NO:19:

( i ) SEQUENCE CHARACTERISTICS:
    ( A ) LENGTH: 12 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:19:

CCCGGGTCTA GA      1 2

( 2 ) INFORMATION FOR SEQ ID NO:20:

( i ) SEQUENCE CHARACTERISTICS:
    ( A ) LENGTH: 41 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:20:

CCCGGGTCTA GACCARNNNN YTGGTAGCGT CAACTCTCGA G      4 1

( 2 ) INFORMATION FOR SEQ ID NO:21:

( i ) SEQUENCE CHARACTERISTICS:
    ( A ) LENGTH: 12 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:21:

CCANNNNNNT GG      1 2

( 2 ) INFORMATION FOR SEQ ID NO:22:

( i ) SEQUENCE CHARACTERISTICS:
   ( A ) LENGTH: 12 base pairs
   ( B ) TYPE: nucleic acid
   ( C ) STRANDEDNESS: single
   ( D ) TOPOLOGY: linear ( x i ) SEQUENCE DESCRIPTION: SEQ ID NO:22:

CCANNNNNNT GG                                    12

( 2 ) INFORMATION FOR SEQ ID NO:23:

( i ) SEQUENCE CHARACTERISTICS:
      ( A ) LENGTH: 15 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:23:

GACGCNNNNN NNNNN                                 15

( 2 ) INFORMATION FOR SEQ ID NO:24:

( i ) SEQUENCE CHARACTERISTICS:
      ( A ) LENGTH: 15 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:24:

NNNNNNNNNN GCGTC                                 15

( 2 ) INFORMATION FOR SEQ ID NO:25:

( i ) SEQUENCE CHARACTERISTICS:
      ( A ) LENGTH: 25 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:25:

GTCGACAGTT GACGCTACCA YNNNN                      25

( 2 ) INFORMATION FOR SEQ ID NO:26:

( i ) SEQUENCE CHARACTERISTICS:
      ( A ) LENGTH: 21 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:26:

RTGGTAGCGT CAACTGTCGA C                          21

( 2 ) INFORMATION FOR SEQ ID NO:27:

( i ) SEQUENCE CHARACTERISTICS:
      ( A ) LENGTH: 20 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:27:

GCTAGCTCTA GACCAYNNNN                            20

( 2 ) INFORMATION FOR SEQ ID NO:28:

( i ) SEQUENCE CHARACTERISTICS:
      ( A ) LENGTH: 16 base pairs ( B ) TYPE: nucleic acid
( C ) STRANDEDNESS: single
( D ) TOPOLOGY: linear ( x i ) SEQUENCE DESCRIPTION: SEQ ID NO:28:

RTGGTCTAGA GCTAGC                                                                                    16

( 2 ) INFORMATION FOR SEQ ID NO:29:

( i ) SEQUENCE CHARACTERISTICS:
      ( A ) LENGTH: 25 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:29:

CTCGAGAGTT GACGCTACCA RNNNN                                                                          25

( 2 ) INFORMATION FOR SEQ ID NO:30:

( i ) SEQUENCE CHARACTERISTICS:
      ( A ) LENGTH: 21 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:30:

YTGGTAGCGT CAACTCTCGA G                                                                              21

( 2 ) INFORMATION FOR SEQ ID NO:31:

( i ) SEQUENCE CHARACTERISTICS:
      ( A ) LENGTH: 20 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:31:

CCCGGGTCTA GACCARNNNN                                                                                20

( 2 ) INFORMATION FOR SEQ ID NO:32:

( i ) SEQUENCE CHARACTERISTICS:
      ( A ) LENGTH: 16 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:32:

YTGGTCTAGA CCCGGG                                                                                    16

( 2 ) INFORMATION FOR SEQ ID NO:33:

( i ) SEQUENCE CHARACTERISTICS:
      ( A ) LENGTH: 20 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:33:

TGGTAGCGTC AACTGTCGAC                                                                                20

( 2 ) INFORMATION FOR SEQ ID NO:34:

( i ) SEQUENCE CHARACTERISTICS:
      ( A ) LENGTH: 15 base pairs
      ( B ) TYPE: nucleic acid
      ( C ) STRANDEDNESS: single (D) TOPOLOGY: linear (xi) SEQUENCE DESCRIPTION: SEQ ID NO:34:

TGGTCTAGAG CTAGC  15

(2) INFORMATION FOR SEQ ID NO:35:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:35:

TGGTAGCGTC AACTCTCGAG  20

(2) INFORMATION FOR SEQ ID NO:36:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:36:

TGGTCTAGAC CCGGG  15

(2) INFORMATION FOR SEQ ID NO:37:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (xi) SEQUENCE DESCRIPTION: SEQ ID NO:37:

GCAGCNNNNN NNN  13

(2) INFORMATION FOR SEQ ID NO:38:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:38:

NNNNNNNNNN NNGCTGC  17

(2) INFORMATION FOR SEQ ID NO:39:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (xi) SEQUENCE DESCRIPTION: SEQ ID NO:39:

GCCNNNNNGG C  11

(2) INFORMATION FOR SEQ ID NO:40:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (x i) SEQUENCE DESCRIPTION: SEQ ID NO:40:

CCANNNNNT GG     12

(2) INFORMATION FOR SEQ ID NO:41:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (x i) SEQUENCE DESCRIPTION: SEQ ID NO:41:

GGATGNNNNN NNNN     14

(2) INFORMATION FOR SEQ ID NO:42:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (x i) SEQUENCE DESCRIPTION: SEQ ID NO:42:

NNNNNNNNN NNNCATCC     18

(2) INFORMATION FOR SEQ ID NO:43:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (x i) SEQUENCE DESCRIPTION: SEQ ID NO:43:

GACGCNNNNN     10

(2) INFORMATION FOR SEQ ID NO:44:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (x i) SEQUENCE DESCRIPTION: SEQ ID NO:44:

NNNNNNNNNN GCGTC     15

(2) INFORMATION FOR SEQ ID NO:45:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (x i) SEQUENCE DESCRIPTION: SEQ ID NO:45:

CCANNNNNTG G     11

(2) INFORMATION FOR SEQ ID NO:46:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (x i) SEQUENCE DESCRIPTION: SEQ ID NO:46:

```
GCATCNNNNN                                                                10
```

( 2 ) INFORMATION FOR SEQ ID NO:47:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:47:

```
NNNNNNNNG ATGC                                                            14
```

( 2 ) INFORMATION FOR SEQ ID NO:48:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:48:

```
GGCCNNNNNG GCC                                                            13
```

METHOD FOR REPLICATING AN ARRAY OF NUCLEIC ACID PROBES

REFERENCE TO RELATED APPLICATIONS

This is a continuation-in-part of U.S. patent application Ser. No. 07/972,012 filed Nov. 6, 1992 now U.S. Pat. No. 5,503,980.

RIGHTS IN THE INVENTION

This invention was made with support from the Department of Energy under grant number PO4591610 and the United States government has certain rights in this invention.

BACKGROUND OF THE INVENTION

1. Field of the Invention

This invention relates to methods for sequencing nucleic acids by positional hybridization and to procedures combining these methods with more conventional sequencing techniques and with other molecular biology techniques including techniques utilized in PCR (polymerase chain reaction) technology. Useful applications include the creation of probes and arrays of probes for detecting, identifying, purifying and sequencing target nucleic acids in biological samples. The invention is also directed to novel methods for the replication of probe arrays, to the replicated arrays, to diagnostic aids comprising nucleic acid probes and arrays useful for screening biological samples for target nucleic acids and nucleic acid variations.

2. Description of the Background

Since the recognition of nucleic acid as the carrier of the genetic code, a great deal of interest has centered around determining the sequence of that code in the many forms which it is found. Two landmark studies made the process of nucleic acid sequencing, at least with DNA, a common and relatively rapid procedure practiced in most laboratories. The first describes a process whereby terminally labeled DNA molecules are chemically cleaved at single base repetitions (A. M. Maxam and W. Gilbert, Proc. Natl. Acad. Sci. USA 74:560–564, 1977). Each base position in the nucleic acid sequence is then determined from the molecular weights of fragments produced by partial cleavages. Individual reactions were devised to cleave preferentially at guanine, at adenine, at cytosine and thymine, and at cytosine alone. When the products of these four reactions are resolved by molecular weight, using, for example, polyacrylamide gel electrophoresis, DNA sequences can be read from the pattern of fragments on the resolved gel.

The second study describes a procedure whereby DNA is sequenced using a variation of the plus-minus method (F. Sanger et al., Proc. Natl. Acad. Sci. USA 74:5463–67, 1977). This procedure takes advantage of the chain terminating ability of dideoxynucleoside triphosphates (ddNTPs) and the ability of DNA polymerase to incorporate ddNTP with nearly equal fidelity as the natural substrate of DNA polymerase, deoxynucleosides triphosphates (dNTPs). A primer, usually an oligonucleotide, and a template DNA are incubated together in the presence of a useful concentration of all four dNTPs plus a limited amount of a single ddNTP. The DNA polymerase occasionally incorporates a dideoxynucleotide which terminates chain extension. Because the dideoxynucleotide has no 3'-hydroxyl, the initiation point for the polymerase enzyme is lost. Polymerization produces a mixture of fragments of varied sizes, all having identical 3' termini. Fractionation of the mixture by, for example, polyacrylamide gel electrophoresis, produces a pattern which indicates the presence and position of each base in the nucleic acid. Reactions with each of the four ddNTPs allows one of ordinary skill to read an entire nucleic acid sequence from a resolved gel.

Despite their advantages, these procedures are cumbersome and impractical when one wishes to obtain megabases of sequence information. Further, these procedures are, for all practical purposes, limited to sequencing DNA. Although variations have developed, it is still not possible using either process to obtain sequence information directly from any other form of nucleic acid.

A new method of sequencing has been developed which overcomes some of the problems associated with current methodologies wherein sequence information is obtained in multiple discrete packages. Instead of having a particular nucleic acid sequenced one base at a time, groups of contiguous bases are determined simultaneously by hybridization. There are many advantages including increased speed, reduced expense and greater accuracy.

Two general approaches of sequencing by hybridization have been suggested. Their practicality has been demonstrated in pilot studies. In one format, a complete set of $4^n$ nucleotides of length n is immobilized as an ordered array on a solid support and an unknown DNA sequence is hybridized to this array (K. R. Khrapko et al., J. DNA Sequencing and Mapping 1:375–88, 1991). The resulting hybridization pattern provides all n-tuple words in the sequence. This is sufficient to determine short sequences except for simple tandem repeats.

In the second format, an array of immobilized samples is hybridized with one short oligonucleotide at a time (Z. Strezoska et al., Proc. Natl. Acad. Sci. USA 88:10,089–93, 1991). When repeated $4^n$ times for each oligonucleotide of length n, much of the sequence of all the immobilized samples would be determined. In both approaches, the intrinsic power of the method is that many sequenced regions are determined in parallel. In actual practice the array size is about $10^4$ to $10^5$.

Another powerful aspect of the method is that information obtained is quite redundant, especially as the size of the nucleic acid probe grows. Mathematical simulations have shown that the method is quite resistant to experimental errors and that far fewer than all probes are necessary to determine reliable sequence data (P. A. Pevzner et al., J. Biomol. Struc. & Dyn. 9:399–410, 1991; W. Bains, Genomics 11:295–301, 1991).

In spite of an overall optimistic outlook, there are still a number of potentially severe drawbacks to actual implementation of sequencing by hybridization. First and foremost among these is that $4^n$ rapidly becomes quite a large number if chemical synthesis of all of the oligonucleotide probes is actually contemplated. Various schemes of automating this synthesis and compressing the products into a small scale array, a sequencing chip, have been proposed.

A second drawback is the poor level of discrimination between a correctly hybridized, perfectly matched duplexes, and an end mismatch. In part, these drawbacks have been addressed at least to a small degree by the method of continuous stacking hybridization as reported by a Khrapko et al. (FEBS Lett. 256:118–22, 1989). Continuous stacking hybridization is based upon the observation that when a single-stranded oligonucleotide is hybridized adjacent to a double-stranded oligonucleotide, the two duplexes are mutually stabilized as if they are positioned side-to-side due to a stacking contact between them. The stability of the interaction decreases significantly as stacking is disrupted by nucleotide displacement, gap, or terminal mismatch. Internal mismatches are presumably ignorable because their thermodynamic stability is so much less than perfect matches. Although promising, a related problem arises which is the inability to distinguish between weak, but correct duplex formation, and simple background such as non-specific adsorption of probes to the underlying support matrix.

A third drawback is that detection is monochromatic. Separate sequential positive and negative controls must be run to discriminate between a correct hybridization match, a mis-match, and background.

A fourth drawback is that ambiguities develop in reading sequences longer than a few hundred base pairs on account of sequence recurrences. For example, if a sequence the same length of the probe recurs three times in the target, the sequence position cannot be uniquely determined. The locations of these sequence ambiguities are called branch points.

A fifth drawback is the effect of secondary structures in the target nucleic acid. This could lead to blocks of sequences that are unreadable if the secondary structure is more stable than occurs on the complimentary strand.

A final drawback is the possibility that certain probes will have anomalous behavior and for one reason or another, be recalcitrant to hybridization under whatever standard sets of conditions ultimately used. A simple example of this is the difficulty in finding matching conditions for probes rich in G/C content. A more complex example could be sequences with a high propensity to form triple helices. The only way to rigorously explore these possibilities is to carry out extensive hybridization studies with all possible oligonucleotides of length n, under the particular format and conditions chosen. This is clearly impractical if many sets of conditions are involved.

Among the early publication which appeared discussing sequencing by hybridization, E. M. Southern (PCT application no. WO 89/10977, published Nov. 16, 1989; which is hereby specifically incorporated by reference), described methods whereby unknown, or target, nucleic acids are labeled, hybridized to a set of nucleotides of chosen length on a solid support, and the nucleotide sequence of the target determined, at least partially, from knowledge of the sequence of the bound fragments and the pattern of hybridization observed. Although promising, as a practical matter, this method has numerous drawbacks. Probes are entirely single-stranded and binding stability is dependant upon the size of the duplex. However, every additional nucleotide of the probe necessarily increases the size of the array by four fold creating a dichotomy which severly restricts its plausible use. Further, there is an inability to deal with branch point ambiguities or secondary structure of the target, and hybridization conditions will have to be tailored or in some way accounted for for each binding event.

R. Drmanac et al. (U.S. Pat. No. 5,202,231; which is specifically incorporated by reference) is directed to methods for sequencing by hybridization using sets of oligonucleotide probes with randon sequences. These probes, although useful, suffer from some of the same drawbacks as the methodology of Southern (1989), and like Southern, fail to recognize the advantages of stacking interactions.

K. R. Khrapko et al. (FEBS Lett. 256:118–22, 1989; and J. DNA Sequencing and Mapping 1:357–88, 1991) attempt to address some of these problems using a technique referred to as continuous stacking hybridization. With continuous stacking, conceptually, the entire sequence of a target nucleic acid can be determined. Basically, the target is hybridized to an array of probes, again single-stranded, denatured from the array, and the dissociation kinetics of denaturation analyzed to determine the target sequence. Although also promising, discrimination between matches and mis-matches (and simple background) is low, and further, as hybridization conditions are inconstant for each duplex, discrimination becomes increasingly reduced with increasing target complexity.

SUMMARY OF THE INVENTION

The present invention overcomes the problems and disadvantages associated with current strategies and designs and provides new methods for rapidly and accurately determining the nucleotide sequence of a nucleic acid by the herein described methods of positional sequencing by hybridization.

One embodiment of the invention is directed to arrays of $R^4$ different nucleic acid probes wherein each probe comprises a double-stranded portion of length D, a terminal single-stranded portion of length S, and a random nucleotide sequence within the single-stranded portion of length R. These arrays may be bound to solid supports and are useful for determining the nucleotide sequence of unknown nucleic acids and for the detection, identification and purification of target nucleic acids in biological samples.

Another embodiment of the invention is directed to methods for creating arrays of probes comprising the steps of synthesizing a first set of nucleic acids each comprising a constant sequence of length C at the 3'-terminus, and a random sequence of length R at the 5'-terminus, synthesizing a second set of nucleic acids each comprising a sequence complimentary to the constant sequence of the first nucleic acid, and hybridizing the first set with the second set to form the array.

Another embodiment of the invention is directed to methods for creating arrays of probes comprising the steps of synthesizing a set of nucleic acids each containing a random internal sequence of length R flanked by the cleavage sites of a restriction enzyme, synthesizing a set of primers each compliementary to a non-random sequence of the nucleic acid, hybridizing the two sets together to form hybrids, extending the sequence of the primer by polymerization using the nucleic acid as a template, and cleaving the hybrids with the restriction enzyme to form an array of probes with a double-stranded portion and a single-stranded portion and with the random sequence within the single stranded portion.

Another embodiment of the invention is directed to replicated arrays and methods for replicating arrays of probes, preferably on a solid support, comprising the steps of synthesizing an array of nucleic acids each comprising a constant sequence of length C at a 3'-terminus and a random sequence of length R at a 5'-terminus, fixing the array to a first solid support, synthesizing a set of nucleic acids each comprising a sequence complimentary to the constant region of the array, hybridizing the nucleic acids of the set with the array, enzymatically extending the nucleic acids of the set using the random sequences of the array as templates, denaturing the set of extended nucleic acids, and fixing the denatured nucleic acids of the set to a second solid support to create the replicated array of probes. The replicated array may be single-stranded or double-stranded, it may be fixed to a solid support or free in solution, and it is useful for sequencing, detecting or simply identifying target nucleic acids.

The array is also useful for the purification of nucleic acid from a complex mixture for later identification and/or sequencing. A purification array comprises sufficient numbers of probes to hybridize and thereby effectively capture the target sequences from a complex sample. The hybridized array is washed to remove non-target nucleic acids and any other materials which may be present and the target sequences eluted by denaturing. From the elution, purified or semi-purified target sequences are obtained and collected. This collection of target sequences can then be subjected to normal sequencing methods or sequenced by the methods described herein.

Another embodiment of the invention is directed to nucleic acid probes and methods for creating nucleic acid probes comprising the steps of synthesizing a plurality of single-stranded first nucleic acids and a plurality of longer single-stranded second nucleic acids wherein each each second nucleic acid comprises a random terminal sequence and a sequence complimentary to a sequence of the first nucleic acids, hybridizing the first nucleic acids to the second to form partial duplexes having a double-stranded portion and a single-stranded portion with the random sequence within the single-stranded portion, hybridizing a target nucleic acid to the partial duplexes, optionally ligating the hybridized target to the first nucleic acid of the partial duplexes, isolating the second nucleic acid from the ligated duplexes, synthesizing a plurality of third nucleic acids each complimentary to the constant sequence of the second nucleic acid, and hybridizing the third nucleic acids with the isolated second nucleic acids to create the nucleic acid probe. Alternatively, after formation of the partial duplexes, the target is ligated as before and hybridized with a set of oligonucleotides comprising random sequences. These oligonucleotides are ligated to the second nucleic acid, the second nucleic acid is isolated, another plurality of first nucleic acids are synthesized, and the first nucleic acids are hybridized to the oligonucleotide ligated second nucleic acids to form the probe. Ligation allows for hybridization to be performed under a single set of hybridization conditions. Probes may be fixed to a solid support and may also contain enzyme recognition sites within their sequences.

Another embodiment of the invention is directed to diagnostic aids and methods utilizing probe arrays for the detection and identification of target nucleic acids in biological samples and to methods for using the diagnostic aids to screen biological samples. Diagnostic aids as described are also useful for the purification of identified targets and, if desired, for their sequencing. These aids comprise probes, solid supports, labels, necessary reagents and the biological samples.

Other advantages of the invention are set forth in part in the description which follows, and in part, will be obvious from this description, or may be learned from the practice of this invention. The accompanying drawings which are incorporated in and constitute a part of this specification, illustrate and, together with this description, serve to explain the principle of the invention.

BRIEF DESCRIPTION OF THE DRAWINGS

FIG. 1 Energetics of stacking hybridization. Structures consist of a long target and a probe of length n. The top three sample are ordinary hybridization and the bottom three are stacking hybridization.

FIG. 9 Four color analysis of sequence extensions of the 3' end of a probe using three labeled nucleoside triphosphates and one unlabeled chain terminator.

DESCRIPTION OF THE INVENTION

Figure 2A:
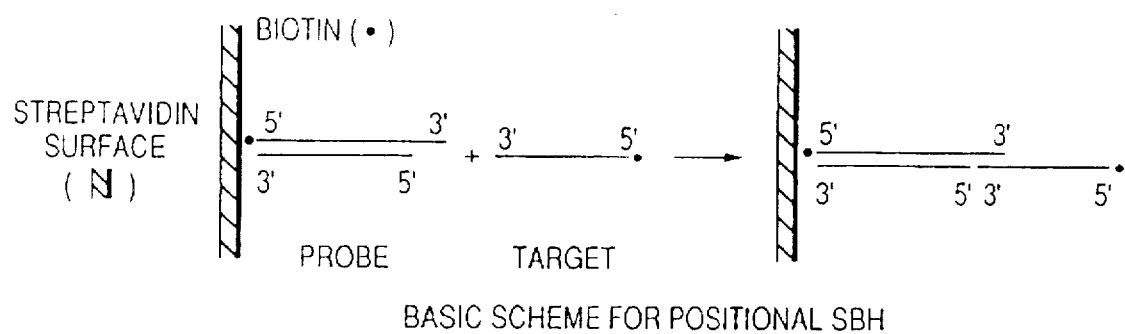
FIG. 2 (A) The first step of the basic scheme for positional sequencing by hybridization depicting the hybridization of target nucleic acid with probe forming a 5' overhang of the target.
(B) The first step of the alternate scheme for positional sequencing by hybridization depicting the hybridization of target nucleic acid with probe forming a 3' overhang of the probe.

The present invention overcomes the problems and disadvantages associated with current strategies and designs and provides new methods and probes, new diagnostic aids and methods for using the diagnostic aids, and new arrays and methods for creating arrays of probes to detect, identify, purify and sequence target nucleic acids. Nucleic acids of the invention include sequences of deoxyribonucleic acid (DNA) or ribonucleic acid (RNA) which may be isolated from natural sources, recombinantly produced, or artificially synthesized. Preferred embodiments of the present invention is probe synthesized using traditional chemical synthesis, using the more rapid polymerase chain reaction (PCR) technology, or using a combination of these two methods.

Nucleic acids of the invention further encompass polyamide nucleic acid (PNA) or any sequence of what are commonly referred to as bases joined by a chemical backbone that have the ability to base pair or hybridize with a complimentary chemical structure. The bases of DNA, RNA, and PNA are purines and pyrimidines linearly linked to a chemical backbone. Common chemical backbone structures are deoxyribose phosphate and ribose phosphate. Recent studies demonstrated that a number of additional structures may also be effective, such as the polyamide backbone of PNA (P. E. Nielsen et al., Sci. 254:1497-1500, 1991).

The purines found in both DNA and RNA are adenine and guanine, but others known to exist are xanthine, hypoxanthine, 2- and 1-diaminopurine, and other more modified bases. The pyrimidines are cytosine, which is common to both DNA and RNA, uracil found predominantly in RNA, and thymidine which occurs exclusively in DNA. Some of the more atypical pyrimidines include methylcytosine, hydroxymethyl-cytosine, methyluracil, hydroxymethyluracil, dihydroxypentyluracil, and other base modifications. These bases interact in a complimentary fashion to form base-pairs, such as, for example, guanine with cytosine and adenine with thymidine. However, this invention also encompasses situations in which there is nontraditional base pairing such as Hoogsteen base pairing which has been identified in certain tRNA molecules and postulated to exist in a triple helix.

One embodiment of the invention is directed to a method for determining a nucleotide sequence by positional hybridization comprising the steps of (a) creating a set of nucleic acid probes wherein each probe has a double-stranded portion, a single-stranded portion, and a random sequence within the single-stranded portion which is determinable, (b) hybridizing a nucleic acid target which is at least partly single-stranded to the set of nucleic acid probes, and (c) determining the nucleotide sequence of the target which hybridized to the single-stranded portion of any probe. The set of nucleic acid probes and the target nucleic acid may comprise DNA, RNA, PNA, or any combination thereof, and may be derived from natural sources, recombinant sources, or be synthetically produced. Each probe of the set of nucleic acid probes has a double-stranded portion which is preferably about 10 to 30 nucleotides in length, a single-stranded portion which is preferably about 4 to 20 nucleotides in length, and a random sequence within the single-stranded portion which is preferably about 4 to 20 nucleotides in length and more preferably about 5 nucleotides in length. A principle advantage of this probe is in its structure. Hybridization of the target nucleic acid is encouraged due to the favorable thermodynamic conditions established by the presence of the adjacent double-strandedness of the probe. An entire set of probes contains at least one example of every possible random nucleotide sequence.

By way of example only, if the random portion consisted of a four nucleotide sequence ($R=4$) of adenine, guanine, thymine, and cystosine, the total number of possible combinations ($4^R$) would be $4^4$ or 256 different nucleic acid probes. If the number of nucleotides in the random sequence was five, the number of different probes within the set would be $4^5$ or 1,024. This becomes a very large number indeed when considering sequences of 20 nucleotides or more.

However, to determine the complete sequence of a nucleic acid target, the set of probes need not contain every possible combination of nucleotides of the random sequence to be encompassed by the method of this invention. This variation of the invention is based on the theory of degenerated probes proposed by S. C. Macevicz (International Patent Application, US89-04741, published 1989, and herein specifically incorporated by reference). The probes are divided into four subsets. In each, one of the four bases is used at a defined number of positions and all other bases except that one on the remaining positions. Probes from the first subset contain two elements, A and non-A (A=adenosine). For a nucleic acid sequence of length k, there are $4(2^k-1)$, instead of $4^k$ probes. Where k=8, a set of probes would consist of only 1020 different members instead of the entire set of 65,536. The savings in time and expense would be considerable. In addition, it is also a method of the present invention to utilize probes wherein the random nucleotide sequence contains gapped segments, or positions along the random sequence which will base pair with any nucleotide or at least not interfere with adjacent base pairing.

Hybridization between complimentary bases of DNA, RNA, PNA, or combinations of DNA, RNA and PNA, occurs under a wide variety of conditions such as variations in temperature, salt concentration, electrostatic strength, and buffer composition. Examples of these conditions and methods for applying them are described in *Nucleic Acid Hybridization: A Practical Approach* (B. D. Hames and S. J. Higgins, editors, IRL Press, 1985), which is herein specifically incorporated by reference. It is preferred that hybridization takes place between about 0° C. and about 70° C., for periods of from about 5 minutes to hours, depending on the nature of the sequence to be hybridized and its length. For example, typical hybridization conditions for a mixture of two 20-mers is to bring the mixture to 68° C. and let cool to room temperature (22° C.) for five minutes or at very low temperatures such as 2° C. in 2 microliters. It is also preferred that hybridization between nucleic acids be facilitated using buffers such as saline, Tris-EDTA (TE), Tris-HCl and other aqueous solutions, certain reagents and chemicals. Preferred examples of these reagents include single-stranded binding proteins such as Rec A protein, T4 gene 32 protein, *E. coli* single-stranded binding protein, and major or minor nucleic acid groove binding proteins. Preferred examples of other reagents and chemicals include divalent ions, polyvalent ions, and intercalating substances such as ethidium bromide, actinomycin D, psoralen, and angelicin.

The nucleotide sequence of the random portion of each probe is determinable by methods which are well-known in the art. Two methods for determining the sequence of the nucleic acid probe are by chemical cleavage, as disclosed by Maxam and Gilbert (1977), and by chain extension using ddNTPs, as disclosed by Sanger et al. (1977), both of which are herein specifically incorporated by reference. Alternatively, another method for determining the nucleotide sequence of a probe is to individually synthesize each member of a probe set. The entire set would comprise every possible sequence within the random portion or some smaller portion of the set. The method of the present invention could then be conducted with each member of the set. Another procedure would be to synthesize one or more sets of nucleic acid probes simultaneously on a solid support. Preferred examples of a solid support include a plastic, a ceramic, a metal, a resin, a gel, and a membrane. A more preferred embodiment comprises a two-dimensional or three-dimensional matrix, such as a gel, with multiple probe binding sites, such as a hybridization chip as described by Pevzner et al. (J. Biomol. Struc. & Dyn. 9:399–410, 1991), and by Maskos and Southern (Nuc. Acids Res. 20:1679–84, 1992), both of which are herein specifically incorporated by reference. Nucleic acids are bound to the solid support by covalent binding such as by conjugation with a coupling agent, or by non-covalent binding such as an electrostatic interaction or antibody-antigen coupling. Typical coupling agents include biotin/streptavidin, *Staphylococcus aureus* protein A/IgG antibody $F_c$ fragment, and streptavidin/protein A chimeras (T. Sano and C. R. Cantor, Bio/Technology 9:1378–81, 1991).

Hybridization chips can be used to construct very large probe arrays which are subsequently hybridized with a target nucleic acid. Analysis of the hybridization pattern of the chip provides an immediate fingerprint identification of the target nucleotide sequence. Patterns can be manually or computer analyzed, but it is clear that positional sequencing by hybridization lends itself to computer analysis and automation. Algorithms and software have been developed for sequence reconstruction which are applicable to the methods described herein (R. Drmanac et al., J. Biomol. Struc. & Dyn. 5:1085–1102, 1991; P. A. Pevzner, J. Biomol. Struc. & Dyn. 7:63–73, 1989, both of which are herein specifically incorporated by reference).

Preferably, target nucleic acids are labeled with a detectable label. Label may be incorporated at a 5' terminal site, a 3' terminal site, or at an internal site within the length of the nucleic acid. Preferred detectable labels include a radioisotope, a stable isotope, an enzyme, a fluorescent chemical, a luminescent chemical, a chromatic chemical, a metal, an electric charge, or a spatial structure. There are many procedures whereby one of ordinary skill can incorporate detectable label into a nucleic acid. For example, enzymes used in molecular biology will incorporate radioisotope labeled substrate into nucleic acid. These include polymerases, kinases, and transferases. The labeling isotope is preferably, $^{32}P$, $^{35}S$, $^{14}C$, or $^{125}I$.

Label may be directly or indirectly detected using scintillation fluid or a PhosphorImager, chromatic or fluorescent labeling, or mass spectrometry. Other, more advanced methods of detection include evanescent wave detection of surface plasmon resonance of thin metal film labels such as gold, by, for example, the BIAcore sensor sold by Pharmacia, or other suitable biosensors. Alternatively, the probe may be labeled and the target nucleic acid detected, identified and possibly sequenced from interaction with the labeled probe. For example, a labeled probe or array of probes may be fixed to a solid support. From an analysis of the binding observed after hybridization with a biological sample containing nucleic acid, the target nucleic acid is identified.

Another embodiment of the invention is directed to methods for determining a sequence of a nucleic acid comprising the steps of labeling the nucleic acid with a first detectable label at a terminal site, labeling the nucleic acid with a second detectable label at an internal site, identifying the nucleotide sequences of portions of the nucleic acid, determining the relationship of the nucleotide sequence portions to the nucleic acid by comparing the first detectable label and the second detectable label, and determining the nucleotide sequence of the nucleic acid. Fragments of target nucleic acids labeled both terminally and internally can be distinguished based on the relative amounts of each label within respective fragments. Fragments of a target nucleic acid terminally labeled with a first detectable label will have the same amount of label as fragments which include the labeled terminus. However, theses fragments will have variable amounts of the internal label directly proportional to their size and distance for the terminus. By comparing the relative amount of the first label to the relative amount of the second label in each fragment, one of ordinary skill is able to determine the position of the fragment or the position of the nucleotide sequence of that fragment within the whole nucleic acid.

Figure 11:
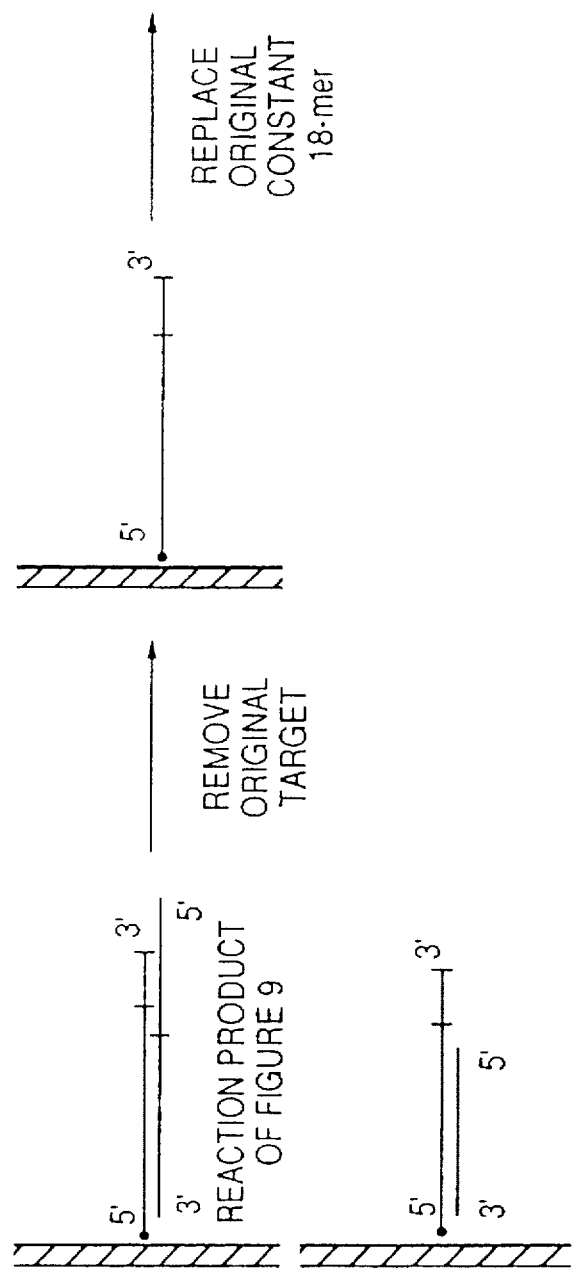
FIG. 11 Preparation of a customized probe containing a 10 base pair sequence that was present in the original target nucleic acid.

Another embodiment of the invention is directed to methods for determining a nucleotide sequence by hybridization comprising the steps of creating a set of nucleic acid probes wherein each probe has a double-stranded portion, a single-stranded portion, and a random sequence within the single-stranded portion which is determinable, hybridizing a nucleic acid target which is at least party single-stranded to the set, ligating the hybridized target to the probe, and determining the nucleic sequence of the target which is hybridized to the single-stranded portion of any probe. This embodiment adds a step wherein the hybridized target is ligated to the probe. Ligation of the target nucleic acid to the complimentary probe increases fidelity of hybridization and allows for incorrectly hybridized target to be easily washed from correctly hybridized target (FIG. 11). More importantly, the addition of a ligation step allows for hybridization to be performed under a single set of hybridization conditions. For example, hybridization temperature is preferably between about 22°–37° C., the salt concentration useful is preferably between about 0.05–0.5M, and the period of hybridization is between about 1–14 hours. This is not possible using the methodologies of the current procedures which do not employ a ligation step and represents a very substantial improvement. Ligation can be accomplished using a eukaryotic derived or a prokaryotic derived ligase. Preferred is T4 DNA or RNA ligase. Methods for use of these and other nucleic acid modifying enzymes are described in *Current Protocols in Molecular Biology* (F. M. Ausubel et al., editors, John Wiley & Sons, 1989), which is herein specifically incorporated by reference.

There are a number of distinct advantages to the incorporation of a ligation step. First and foremost is that one can use identical hybridization conditions for hybridization. Variation of hybridization conditions due to base composition are no longer relevant as nucleic acids with high A/T or G/C content ligate with equal efficiency. Consequently, discrimination is very high between matches and mismatches, much higher than has been achieved using other methodologies such as Southern (1989) wherein the effects of G/C content were only somewhat neutralized in high concentrations of quarternary or tertiary amines (e.g., 3M tetramethyl ammonium chloride in Drmanac et al., 1993).

Another embodiment of the invention is directed to methods for determining a nucleotide sequence by hybridization which comprises the steps of creating a set of nucleic acid probes wherein each probe has a double-stranded portion, a single-stranded portion, and a random sequence within the single-stranded portion which is determinable, hybridizing a target nucleic acid which is at least partly single-stranded to the set of nucleic acid probes, enzymatically extending a strand of the probe using the hybridized target as a template, and determining the nucleotide sequence of the single-stranded portion of the target nucleic acid. This embodiment of the invention is similar to the previous embodiment, as broadly described herein, and includes all of the aspects and advantages described therein. An alternative embodiment also includes a step wherein hybridized target is ligated to the probe. Ligation increases the fidelity of the hybridization and allows for a more stringent wash step wherein incorrectly hybridized, unligated target can be removed and further, allows for a single set of hybridization conditions to be employed. Most nonligation techniques including Southern (1989), Drmanac et al. (1993), and Khrapko et al. (1989 and 1991), are only accurate, and only marginally so, when hybriizations are performed under optimal conditions which vary with the G/C content of each interaction. Preferable condiions comprise a hybridization temperature of between about 22°–37° C., a salt concentration of betwen about 0.05–0.5M, and a hybridization period of between about 1–14 hours.

Hybridization produces either a 5' overhang or a 3' overhang of target nucleic acid. Where there is a 5' overhang, a 3-hydroxyl is available on one strand of the probe from which nucleotide addition can be initiated. Preferred enzymes for this process include eukaryotic or prokaryotic polymerases such as T3 or T7 polymerase, Klenow fragment, or Taq polymerase. Each of these enzymes are readily available to those of ordinary skill in the art as are procedures for their use (*Current Protocols in Molecular Biology*).

Hybridized probes may also be enzymatically extended a predetermined length. For example, reaction condition can be established wherein a single dNTP or ddNTP is utilized as substrate. Only hybridized probes wherein the first nucleotide to be incorporated is complimentary to the target sequence will be extended, thus, providing additional hybridization fidelity and additional information regarding the nucleotide sequence of the target. Sanger (1977) or Maxam and Gilbert (1977) sequencing can be performed which would provide further target sequence data. Alternatively, hybridization of target to probe can produces 3' extensions of target nucleic acids. Hybridized probes can be extended using nucleoside biphosphate substrates or short sequences which are ligated to the 5' terminus.

Another embodiment of the invention is directed to a method for determining a nucleotide sequence of a target by hybridization comprising the steps of creating a set of nucleic acid probes wherein each probe has a double-stranded portion, a single-stranded portion, and a random nucleotide sequence within the single-stranded portion which is determinable, cleaving a plurality of nucleic acid targets to form fragments of various lengths which are at least partly single-stranded, hybridizing the single-stranded region of the fragments with the single-stranded region of the probes, identifying the nucleotide sequences of the hybridized portions of the fragments, and comparing the identified nucleotide sequences to determine the nucleotide sequence of the target. An alternative embodiment includes a further step wherein the hybridized fragments are ligated to the probes prior to identifying the nucleotide sequences of the hybridized portions of the fragments. As described herein, the addition of a ligation step allows for hybridizations to be performed under a single set of hybridization conditions.

In these embodiments, target nucleic acid is partially cleaved forming a plurality of nucleic acid fragments of various lengths, a nested set, which is then hybridized to the probe. It is preferred that cleavage occurs by enzymatic, chemical or physical means. Preferred enzymes for partial cleavage are exonuclease III, S1 nuclease, DNase I, Bal 31, mung bean nuclease, P1 nuclease, lambda exonuclease, restriction endonuclease, and RNase I. Preferred means for chemical cleavage are ultraviolet light induced cleavage, ethidium bromide induced cleavage, and cleavage induced with acid or base. Preferred means for mechanical cleavage are shearing through direct agitation such as vortexing or multiple cycles of freeze-thawing. Procedures for enzymatic, chemical or physical cleavage are disclosed in, for example, *Molecular Cloning: A Laboratory Manual* (T. Maniatis et al., editors, Cold Spring Harbor 1989), which is herein specifically incorporated by reference.

Fragmented target nucleic acids will have a distribution of terminal sequences which is sufficiently broad so that the nucleotide sequence of the hybridized fragments will include the entire sequence of the target nucleic acid. A preferred method is wherein the set of nucleic acid probes is fixed to a solid support. A preferred solid support is a plastic, a ceramic, a metal or magnetic substance, a resin, a film or other polymer, a gel, or a membrane, and it is more preferred that the solid support be a two-dimensional or three-dimensional matrix with multiple probe binding sites such as a hybridization chip as described by K. R. Khrapko et al. (J. DNA Sequencing and Mapping 1:357–88, 1991). It is also preferred wherein the target nucleic acid has a detectable label such as a radioisotope, a stable isotope, an enzyme, a fluorescent chemical, a luminescent chemical, a chromatic chemical, a metal, an electric charge, or a spatial structure.

As an extension of this procedure, it is also possible to use the methods herein described to determine the nucleotide sequence of one or more probes which hybridize with an unknown target sequence. For example, fragmented targets could be terminally or internally labeled, hybridized with a set of nucleic acid probes, and the hybridized sequences of the probes determined. This aspect may be useful when it is cumbersome to determine the sequence of the entire target and only a smaller region of that sequence is of interest.

Another embodiment of the invention is directed a method wherein the target nucleic acid has a first detectable label at a terminal site and a second detectable label at an internal site. The labels may be the same type of label or of different types as long as each can be discriminated, preferably by the same detection method. It is preferred that the first and second detectable labels are chromatic or fluorescent chemicals or molecules which are detectable by mass spectrometry. Using a double-labeling method coupled with analysis by mass spectrometry provides a very rapid and accurate sequencing methodology that can be incorporated in sequencing by hybridization and lends itself very well to automation and computer control.

Another embodiment of the invention is directed to methods for creating a nucleic acid probe comprising the steps of synthesizing a plurality of single-stranded first nucleic acids and an array of longer single-stranded second nucleic acids complimentary to the first nucleic acid with a random terminal nucleotide sequence, hybridizing the first nucleic acids to the second nucleic acids to form hybrids having a double-stranded portion and a single-stranded portion with the random nucleotide sequence within the single-stranded portion, hybridizing a single-stranded nucleic acid target to the hybrids, ligating the hybridized target to the first nucleic acid of the hybrid, isolating the second nucleic acid, and hybridizing the first nucleic acid of step with the isolated second nucleic acid to form a nucleic acid probe. Probes created in this manner are referred to herein as customized probes.

Preferred customized probe comprises a first nucleic acid which is about 15–25 nucleotides in length and the second nucleic acid is about 20–30 nucleotides in length. It is also preferred that the double-stranded portion contain an enzyme recognition site which allows for increased flexibility of use and facilitates cloning, should it at some point become desirable to clone one or more of the probes. It is also preferred if the customized probe is fixed to a solid support, such as, a plastic, a ceramic, a metal, a resin, a film or other polymer, a gel, or a membrane, or possibly a two- or three-dimensional array such as a chip or microchip.

Customized probes, created by the method of this invention, have a wide range of uses. These probes are, first of all, structurally useful for identifying and binding to only those sequences which are homologous to the overhangs. Secondly, the overhangs of these probes possess the nucleotide sequence of interest. No further manipulation is required to carry the sequence of interest to another structure. Therefore, the customized probes greatly lend themselves to use in, for example, diagnostic aids for the genetic screening of a biological sample.

Another embodiment of the invention is directed to arrays of nucleic acid probes wherein each probe comprises a double-stranded portion of length D, a terminal single-stranded portion of length S, and a random nucleotide sequence within the single-stranded portion of length R. Preferably, D is between about 3–20 nucleotides and S is between about 3–20 nucleotides and the entire array is fixed to a solid support which may be composed of plastics, ceramics, metals, resins, polymers and other films, gels, membranes and two-dimensional and three-dimensional matrices such as hybridization chips or microchips. Probe arrays are useful in sequencing and diagnostic applications when the sequence and/or position on a solid support of every probe of the array is known or is unknown. In either case, information about the target nucleic acid may be obtained and the target nucleic acid detected, identified and sequenced as described in the methods described herein. Arrays comprise $4^R$ different probes representing every member of the random sequence of length R, but arrays of less than $4^R$ are also encompassed by the invention.

Another embodiment of the invention is directed to a method for creating probe arrays comprising the steps of synthesizing a first set of nucleic acids each comprising a constant sequence of length C at a 3'-terminus and a random sequence of length R at a 5'-terminus, synthesizing a second set of nucleic acids each comprising a sequence complimentary to the constant sequence of each of the first nucleic acid, and hybridizing the first set with the second set to create the array. Preferably, the nucleic acids of the first set are each between about 15–30 nucleotides in length and the nucleic acids of the second set are each between about 10–25 nucleotides in length. Also preferable is that C is between about 7–20 nucleotides and R is between about 3–10 nucleotides.

Arrays may comprise about $4^R$ different probes, but in certain applications, an entire array of every possible sequence is not necessary and incomplete arrays are acceptable for use. For example, incomplete arrays may be utilized for screening procedures of very rare target nucleic acids where nonspecific hybridization is not expected to be problematic. Further, every member of an array may not be needed when detecting or sequencing smaller nucleic acids where the chance of requiring certain combinations of nucleotides is so low as to be practically nonexistent. Array which are fixed to solid supports are expected to be most useful, although array in solution also have many applications. Solid supports which are useful include plastics such as microtiter plates, beads and microbeads, ceramics, metals where resilience is desired or magnetic beads for ease of isolation, resins, gels, polymers and other films, membranes or chips such as the two- and three-dimensional sequencing chips utilized in sequencing technology.

Alternatively, probe arrays may also be made which are single-stranded. These arrays are created, preferably on a solid support, basically as described, by synthesizing an array of nucleic acids each comprising a constant sequence of length C at a 3'-terminus and a random sequence of length R at a 5'-terminus, and fixing the array to a first solid support. Arrays created in this manner can be quickly and easily transformed into double-stranded arrays by the synthesis and hybridization of a set of nucleic acids with a sequence complimentary to the constant sequence of the replicated array to create a double-stranded replicated array. However, in their present form, single-stranded arrays are very valuable as templates for replication of the array.

Due to the very large numbers of probes which comprise most useful arrays, there is a great deal of time spent in simply creating the array. It requires many hours of nucleic acid synthesis to create each member of the array and many hours of manipulations to place the array in an organized fashion onto any solid support such as those described previously. Once the master array is created, replicated arrays or slaves, can be quickly and easily created by the methods of the invention which take advantage of the speed and accuracy of nucleic acid polymerases. Basically, methods for replicating an array of single-stranded probes on a solid support comprise the steps of synthesizing an array of nucleic acids each comprising a constant sequence of length C at a 3'-terminus and a random sequence of length R at a 5'-terminus, fixing the array to a first solid support, synthesizing a set of nucleic acids each comprising a sequence complimentary to the constant sequence, hybridizing the nucleic acids of the set with the array, enzymatically extending the nucleic acids of the set using the random sequences of the array as templates, denaturing the set of extended nucleic acids, and fixing the denatured nucleic acids of the set to a second solid support to create the replicated array of single-stranded probes, Denaturation of the array can be performed by subjecting the array to heat, for example 90°–100° C. for 2–15 minutes, or highly alkaline conditions, such as by the addition of sodium hydroxide. Denaturation can also be accomplished by adding organic solvents, nucleic acid binding proteins or enzymes which promote denaturation to the array. Preferably, the solid supports are coated with a substance such as streptavidin and the nucleic acid reagents conjugated with biotin. Denaturation of the partial duplex leads to binding of the nucleic acids to the solid support.

Another embodiment of the invention is directed to methods for creating arrays of probes comprising the steps of synthesizing an array of single-stranded nucleic acids each containing a constant sequence at the 3'-terminus, another constant sequence at the 5'-terminus, and a random internal sequence of length R flanked by the cleavage site(s) of a restriction enzyme (on one or both sides), synthesizing an array of primers each compliementary to a portion of the constant sequence of the 3'-terminus, hybridizing the two arrays together to form hybrids, extending the sequence of each primer by polymerization using a sequence of the nucleic acid as a template, and cleaving the extended hybrids with the restriction enzyme to form an array of probes with a double-stranded portion at one terminus, a single-stranded portion containing the random sequence at the opposite terminus. Preferably, the nucleic acids are each between about 10–50 nucleotides in length and R is between about 3–5 nucleotides in length. Any of the restriction enzymes which produce a 3'- or 5'-overhang after cleavage are suitable for use to make the array. Some of the restriction enzymes which are useful in this regard, and their recognition sequences are depicted in Table 1.

TABLE 1

| Restriction Enzyme | Recognition Sequence 5'-Overhang | 3'-Overhang |
|---|---|---|
| AlwN I | 5'-CAG NNN↓CTG<br>3'-GTC↑NNN GAC | |
| Bbv I | 5'-GCAGC(N)₈↓ (SEQ ID NO 37)<br>3'-CGTCG(N)₁₂↑ (SEQ ID NO 38) | |
| Bgl I | 5'-GCCN NNN↓NGGC (SEQ ID NO 39) | |

TABLE 1-continued

| Restriction Enzyme | Recognition Sequence | |
|---|---|---|
| | 5'-Overhang | 3'-Overhang |
| BstX I | 3'CGGN↑NNN NCCG (SEQ ID NO 39) | 5'-CCAN NNNN↓NTGG (SEQ ID NO 40)<br>3'-GGTN↑NNNN NACC (SEQ ID NO 40) |
| Dra III | 5'-CAC NNN↓GTG<br>3'-GTG↑NNN CAC | |
| Fok I | 5'-GGATG(N)₉↓ (SEQ ID NO 41)<br>3'-CCTAC(N)₁₃↑ (SEQ ID NO 42) | |
| Hga I | 5'-GACGC(N)₅↓ (SEQ ID NO 43)<br>3'-CTGCG(N)₁₀↑ (SEQ ID NO 44) | |
| PflM I | | 5'-CCAN NNN↓NTGG (SEQ ID NO 45)<br>3'-GGTN↑NNN NACC (SEQ ID NO 45) |
| SfaN I | 5'-GCATC(N)₅↓ (SEQ ID NO 46)<br>3'-CGTAG(N)₉↑ (SEQ ID NO 47) | |
| Dfi I | | 5'-GGCCN NNN↓NGGCC (SEQ ID NO 48)<br>3'-CCGGN↑NNN NCCGG (SEQ ID NO 48) |

Also prefered is that the array be fixed to a solid support such as a plastic, ceramic, metal, resin, polymer, gel, film, membrane or chip. Fixation can be accomplished by conjugating the reagents for synthesis with a specific binding protein or other similar substance and coating the surface of the support with the binding counterpart (e.g. biotin/streptavidin, F$_c$/protein A, nucleic acid/nucleic acid binding protein).

Alternatively, another similar method for creating an array of probes comprising the steps of synthesizing an array of single-stranded nucleic acids each containing a constant sequence at the 3'-terminus, another constant sequence at the 5'-terminus, and a random internal sequence of length R flanked by the cleavage site(s) of a restriction enzyme (on one or both sides), synthesizing an array of primers with a sequence complimentary to the constant sequence at the 3'-terminus, hybridizing the two arrays together to form hybrids, enzymatically extending the primers using the nucleic acids as templates to form full-length hybrids, cloning the full-length hybrids into vectors such as plasmids or phage, cloning the plasmids into competent bacteria or phage, reisolating the cloned plasmid DNA, amplifying the cloned sequences by multiple polymerase chain reactions, and cleaving the amplified sequences with the restriction enzyme to form the array of probes with a double-stranded portion at one terminus and a single-stranded portion containing the random sequence at the opposite terminus. Using this method the array of probes may have 5'- or 3'-overhangs depending on the cleavage specificity of the restriction enzyme (e.g. Table 1). The array of probes may be fixed to a solid support such as a plastic, ceramic, metal, resin, polymer, film, gel, membranes and chip. Preferably, during PCR amplification, the reagent primers are conjugated with biotin which facilitates eventual binding to a streptavidin coated surface.

Another embodiment of the invention is directed to methods for using customized probes, arrays, and replicated arrays, as described herein, in diagnostic aids to screen biological samples for specific nucleic acid sequences. Diagnostic aids and methods for using diagnostic aids would be very useful when sequence information at a particular locus of, for example, DNA is desired. Single nucleotide mutations or more complex nucleic acid fingerprints can be identified and analyzed quickly, efficiently, and easily. Such an approach would be immediately useful for the detection of individual and family genetic variation, of inherited mutations such as those which cause a disease, DNA dependent normal phenotypic variation, DNA dependent somatic variation, and the presence of heterologous nucleic acid sequences.

Especially useful are diagnostic aids comprising probe arrays. These arrays can make the detection identification, and sequencing of nucleic acids from biological samples exceptionally rapid and allows one to obtain multiple pieces of information from a single sample after performing a single test. Methods for detecting and/or identifying a target nucleic acid in a biological sample comprise the steps of creating an array of probes fixed to a solid support as described herein, labeling the nucleic acid of the biological sample with a detectable label, hybridizing the labeled nucleic acid to the array and detecting the sequence of the nucleic acid from a binding pattern of the label on the array. These methods for creating probe arrays and for rapidly and efficiently replicating those arrays, such as for diagnostic aids, makes the manufacture and commercial application of large numbers of arrays a possibility.

As described, these diagnostic aids are useful to humans, other animals, and even plants for the detection of infections due to viruses, bacteria, fungi or yeast, and for the detection of certain parasites. These detection methods and aids are also useful in the feed and food industries and in the environmental field for the detection, identification and sequencing of nucleic acids associated with samples obtained from environmental sources and from manufacturing products and by-products.

Diagnostic aids comprise specific nucleic acid probes fixed to a solid support to which is added the biological sample. Hybridization of target nucleic acids is determined by adding a detectable label, such as a labeled antibody, which will specifically recognize only hybridized targets or, alternatively, unhybridized target is washed off and labeled target specific antibodies are added. In either case, appearance of label on the solid support indicates the presence of nucleic acid target hybridized to the probe and consequently, within the biological sample.

Customized probes may also prove useful in prophylaxis or therapy by directing a drug, antigen, or other substance to a nucleic acid target with which it will hybridize. The substance to be targeted can be bound to the probe so as not to interfere with possible hybridization. For example, if the probe was targeted to a viral nucleic acid target, an effective antiviral could be bound to the probe which will then be able to specifically carry the antiviral to infected cells. This would be especially useful when the treatment is harmful to normal cells and precise targeting is required for efficacy.

Another embodiment of the invention is directed to methods for creating a nucleic acid probe comprising the steps of synthesizing a plurality of single-stranded first nucleic acids and an array of longer single-stranded second nucleic acids complimentary to the first nucleic acid with a random terminal nucleotide sequence, hybridizing the first nucleic acids to the second nucleic acids to form hybrids having a double-stranded portion and a single-stranded portion with the random nucleotide sequence within the single-stranded portion, hybridizing a single-stranded nucleic acid target to the hybrids, ligating the hybridized target to the first nucleic acid of the hybrid, hybridizing the ligated hybrid with an array of oligonucleotides with random nucleotide sequences, ligating the hybridized oligonucleotide to the second nucleic acid of the ligated hybrid, isolating the second nucleic acid, and hybridizing another first nucleic acid with the isolated second nucleic acid to form a nucleic acid probe. Preferred is that the first nucleic acid is about 15–25 nucleotides in length, that the second nucleic acid is about 20–30 nucleotides in length, that the constant portion contain an enzyme recognition site, and that the oligonucleotides are each about 4–20 nucleotides in length. Probes may be fixed to a solid support such as a plastic, ceramic, a metal, a resin, a gel, or a membrane. It is preferred that the solid support be a two-dimensional or three-dimensional matrix with multiple probe binding sites such as a hybridization chip. Nucleic acid probes created by the method of the present invention are useful in a diagnostic aid to screen a biological sample for genetic variations of nucleic acid sequences therein.

Another embodiment of the invention is directed to a method for creating a nucleic acid probe comprising the steps of (a) synthesizing a plurality of single-stranded first nucleic acids and a set of longer single-stranded second nucleic acids complimentary to the first nucleic acid with a random terminal nucleotide sequence, (b) hybridizing the first nucleic acids to the second nucleic acids to form hybrids having a double-stranded portion and a single-stranded portion with the random nucleotide sequence in the single-stranded portion, (c) hybridizing a single-stranded nucleic acid target to the hybrids, (d) ligating the hybridized target to the first nucleic acid of the hybrid, (e) enzymatically extending the second nucleic acid using the target as a template, (f) isolating the extended second nucleic acid, and (g) hybridizing the first nucleic acid of step (a) with the isolated second nucleic acid to form a nucleic acid probe. It is preferred that the first nucleic acid is about 15–25 nucleotides in length, that the second nucleic acid is about 20–30 nucleotides in length, and that the double-stranded portion contain an enzyme recognition site. It is also preferred that the probe be fixed to a solid support, such as a plastic, ceramic, a metal, a resin, a gel, or a membrane. A preferred solid support is a two-dimensional or three-dimensional matrix with multiple probe binding sites, such as a hybridization chip. A further embodiment of the present invention is a diagnostic aid comprising the created nucleic acid probe and a method for using the diagnostic aid to screen a biological sample as herein described.

As an extension of this procedure, it is also possible to use the methods herein described to determine the nucleotide sequence of one or more probes which hybridize with an unknown target sequence. For example, Sanger dideoxynucleotide sequencing techniques could be used when enzymatically extending the second nucleic acid using the target as a template and labeled substrate, extended products could be resolved by polyacrylamide gel electrophoresis, and the hybridized sequences of the probes easily read off the gel. This aspect may be useful when it is cumbersome to determine the sequence of the entire target and only a smaller region of that sequence is of interest.

The following examples illustrate embodiments of the invention, but should not be viewed as limiting the scope of the invention.

EXAMPLES

Example 1

Manipulation of DNA in the solid state. Complexes between streptavidin (or avidin) and biotin represent the standard way in which much solid state DNA sequencing or other DNA manipulation is done, and one of the standard ways in which non-radioactive detection of DNA is carried out. Over the past few years streptavidin-biotin technology has expanded in several ways. Several years ago, the gene for streptavidin was cloned and sequenced (C. E. Argarana et al., Nuc. Acids Res. 14:1871, 1986). More recently, using the Studier T7 system, over-expression of the Protein in *E. coli* was achieved (T. Sano and C. R. Cantor, Proc. Natl. Acad. Sci. USA 87:142, 1990). In the last year, mutant streptavidins modified for improved solubility properties and firmer attachment to solid supports was also expressed (T. Sano and C. R. Cantor, Bio/Technology 9:1378–81, 1993). The most relevant of these is core streptavidin, (fully active protein with extraneous N- and C-terminal peptides removed) with 5 cysteine residues attached to the C-terminus. An active protein fusion of streptavidin to two IgG binding domains of staphylococcal A protein was also produced (T. Sano and C. R. Cantor, Bio/Technology 9:1378–81, 1991). This allowed biotinylated DNAs to be attached to specific Immunoglobulin G molecules without the need for any covalent chemistry, and it has led to the development of immuno-PCR, an exceedingly sensitive method for detecting antigens (T. Sano et al., Sci. 258:120–29, 1992).

A protein fusion between streptavidin and metallothionein was recently onstructed (T. Sano et al., Proc. Natl. Acad. Sci. USA, 1992). Both partners in this protein fusion are fully active and these streptavidin-biotin interactions are being used to develop new methods for purification of DNA, including triplex-mediated capture of duplex DNA on magnetic microbeads (T. Ito et al., Proc. Natl. Acad. Sci. USA 89:495–98, 1992) and affinity capture electrophoresis of DNA in agarose (T. Ito et al., G.A.T.A., 1992).

An examination of the potential advantages of stacking hybridization has been carried out by both calculations and pilot experiments. Some calculated $T_m$'s for perfect and mismatched duplexes are shown in FIG. 1. These are based on average base compositions. The calculations were preformed using the equations given by J. G. Wetmur (Crit. Rev. in Biochem. and Mol. Biol. 26:227–59, 1991). In the case of oligonucleotide stacking, these researchers assumed that the first duplex is fully formed under the conditions where the second oligomer is being tested; in practice this may not always be the case. It will, however, be the case for the configuration shown in FIG. 1. The calculations reveal a number of interesting features about stacking hybridization. Note that the binding of a second oligomer next to a pre-formed duplex provides an extra stability equal to about two base pairs. More interesting, still, is the fact that mispairing seems to have a larger consequence on stacking hybridization than it does on ordinary hybridization. This is consistent with the very large effects seen by K. R. Khrapko et al. (J. DNA Sequencing and Mapping 1:375–88, 1991) for certain types of mispairing. Other types of mispairing are less destabilizing, but these can be eliminated by requiring a ligation step. In standard SBH, a terminal mismatch is the least destabilizing event, and thus, leads to the greatest source of ambiguity or background. For an octanucleotide complex, an average terminal mismatch leads to a 6° C. lowering in $T_m$. For stacking hybridization, a terminal mismatch on the side away from the pre-existing duplex, is the least destabilizing event. For a pentamer, this leads to a drop in $T_m$ of 10° C. These considerations indicate that the discrimination power of stacking hybridization in favor of perfect duplexes might be greater than ordinary SBH.

Example 2

Terminal sequencing by positional hybridization. The basic sequencing by hybridization scheme is depicted in FIG. 2. It is different from any other because it uses a duplex oligonucleotide array with 3'-ended single-stranded overhangs. The duplex portion of each DNA shown is constant. Only the overhangs vary, and in principle an array of $4^n$ probes is needed to represent all possible overhangs of length n. The advantage of such an array is that it provides enhanced sequence stringency in detecting the 5' terminal nucleotide of the target DNA because of base stacking between the preformed DNA duplex and the newly formed duplex.

One variable is the length of the single-stranded overhang. The shorter the overhang, the smaller the array of probes potentially useable. Overhangs of five and six have been successfully employed. The nature of the support surface to which the oligonucleotide is attached, the means of its attachment, and the length of the oligonucleotide duplex are also important variables. Initially one 5' end-biotinylated strand of the probe duplex is attached to a solid surface. The technology is already well developed for the attachment of nucleic acids to solid supports, such as streptavidin-coated magnetic microbeads and membranes such as the thin gel system.

Another variable is the nucleic acid capacity of the immobilized spot of probe. This determines the detection sensitivity required and is also important where unlabeled DNA may be present that could hybridize competitively with the desired labeled DNA product. As depicted in FIG. 2A, the 3' overhang of the array can detect the 3'-terminal sequence of the target DNA. These will derive from 5'-end labeled restriction fragments of known DNA sequence cut from vectors so that the target for the immobilized probe will either be at the 3' end, just internal to it, or totally internal. In some subsequent examples, it does not matter whether hybridization is absolutely specific for the 3' end.

Figure 2B:
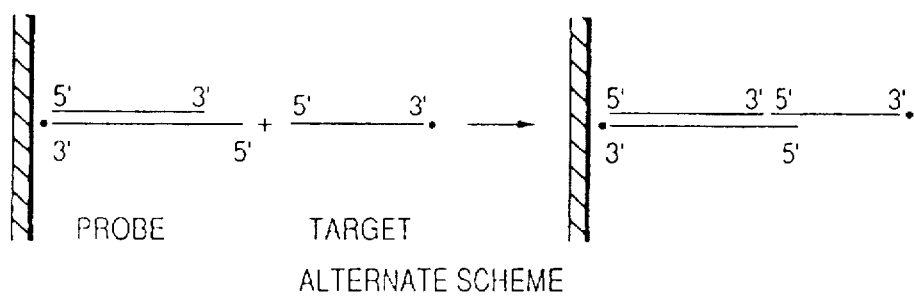

Alternatively, positional sequencing by hybridization of the 5'-end single-stranded overhangs would be equally effective (FIG. 2B). This permits reading of the 5' terminal sequence of the target DNA. However, this approach is not as versatile because it does not allow for the use of polymerases to enhance the length and accuracy of the sequence read.

Example 3

Preparation of model arrays. Following the scheme shown in FIG. 2, in a single synthesis, all 1024 possible single-stranded probes with a constant 18 base stalk followed by a variable 5 base extension can be created. The 18 base extension is designed to contain two restriction enzyme cutting sites. Hga I generates a 5 base, 5' overhang consisting of the variable bases $N_5$. Not I generates a 4 base, 5' overhang at the constant end of the oligonucleotide. The synthetic 23-mer mixture will be hybridized with a complimentary 18-mer to form a duplex which can then be enzymatically extended to form all 1024, 23-mer duplexes. These can be cloned by, for example, blunt end ligation, into a plasmid which lacks Not I sites. Colonies containing the cloned 23-base insert can be selected. Each should be a clone of one unique sequence. DNA minipreps can be cut at the constant end of the stalk, filled in with biotinylated pyrimidines, then cut at the variable end of the stalk to generate the 5 base 5' overhang. The resulting nucleic acid can be fractionated by Qiagen columns (nucleic acid purification columns) to discard the high molecular weight material, and the nucleic acid probe will then be attached to a streptavidin-coated surface. This procedure could easily be automated in a Beckman Biomec or equivalent chemical robot to produce many identical arrays of probes.

The initial array contains about a thousand probes. The particular sequence at any location in the array will not be known. However, the array can be used for statistical evaluation of the signal to noise ratio and the sequence discrimination for different target molecules under different hybridization conditions. Hybridization with known nucleic acid sequences allows for the identification of particular elements of the array. A sufficient set of hybridizations would train the array for any subsequent sequencing task. Arrays are partially characterized until they have the desired properties. For example, the length of the oligonucleotide duplex, the mode of its attachment to a surface, and the hybridization conditions used, can all be varied, using the initial set of cloned DNA probes. Once the sort of array that works best is determined, a complete and fully characterized array can then be constructed by ordinary chemical synthesis.

Example 4

Preparation of specific probe arrays. The major challenge for positional SBH, is to build real arrays of probes, and test the fraction of sequences that actually perform according to expectations. Base composition and base sequence dependence on the effectiveness of hybridization is probably the greatest obstacle to successful implementation of these methods. The use of enzymatic steps, where feasible, may simplify these problems, since, after all, the enzymes do manage to work with a wide variety of DNA sequences in vivo. With positional SBH, one potential trick to compensate for some variations in stability would be to allow the adjacent duplex to vary. Thus, for an A+T rich overhang, one could use a G+C rich stacking duplex, and vice versa.

Four methods for making arrays are tested and evaluated with two major objectives. The first is to produce, rapidly and inexpensively, arrays that will test some of the principles of positional SBH. The second is to develop effective methods for the automated preparation of full arrays needed for production sequencing via positional SBH. Since the first studies indicated that a five base overhang will be sufficient, arrays may only have to have 1024 members. The cost of making all of these compounds is actually quite modest. The constant portion of the probes can be made once, and then extended in parallel, by automated DNA synthesis methods. In the simplest case, this will require the addition of only 5 bases to each of 1024 compounds, which at typical chemical costs of $2 per base will amount to a total of about $10,000.

Moderately dense arrays can be made using a typical x-y robot to spot the biotinylated compounds individually onto a streptavidin-coated surface. Using such robots, it is possible to make arrays of $2 \times 10^4$ samples in 100 to 400 cm² of nominal surface. T array should preferably fit in 10 cm², but even if forced, for unforeseen technical reasons, to compromise on an array ten times or even 50 times less dense, it will be quite suitable for testing the principles of and many of the variations on positional SBH. Commercially available streptavidin-coated beads can be adhered, permanently to plastics like polystyrene, by exposing the plastic first to a brief treatment with an organic solvent like triethylamine. The resulting plastic surfaces have enormously high biotin binding capacity because of the very high surface area that results. This will suffice for radioactively labeled samples.

For fluorescently labeled samples, the background scattering from such a bead-impregnated sample may interfere. In this case, a streptavidin-conjugated glass or plastic surface may be utilized (commercially available from Bios Products). Surfaces are made using commercially available amine-containing surfaces and using commercially available biotin-containing N-hydroxysuccinimide esters to make stable peptide conjugates. The resulting surfaces will bind streptavidin, at one biotin binding site (or at most two, but not more because the approximate 222 symmetry of the protein would preclude this), which would leave other sites available for binding to biotinylated oligonucleotides.

In certain experiments, the need for attaching oligonucleotides to surfaces may be circumvented altogether, and oligonucleotides attached to streptavidin-coated magnetic microbeads used as already done in pilot experiments. The beads can be manipulated in microtitre plates. A magnetic separator suitable for such plates can be used including the newly available compressed plates. For example, the 18 by 24 well plates (Genetix, Ltd.; USA Scientific Plastics) would allow containment of the entire array in 3 plates; this formate is well handled by existing chemical robots. It is preferable to use the more compressed 36 by 48 well formate, so that the entire array would fit on a single plate. The advantages of this approach for all the experiments are that any potential complexities from surface effects can be avoided, and already-existing liquid handling, thermal control, and imaging methods can be used for all the experiments. Thus, this allows the characterization of many of the features of positional SBH before having to invest the time and effort in fabricating instruments, tools and chips.

Figure 14:
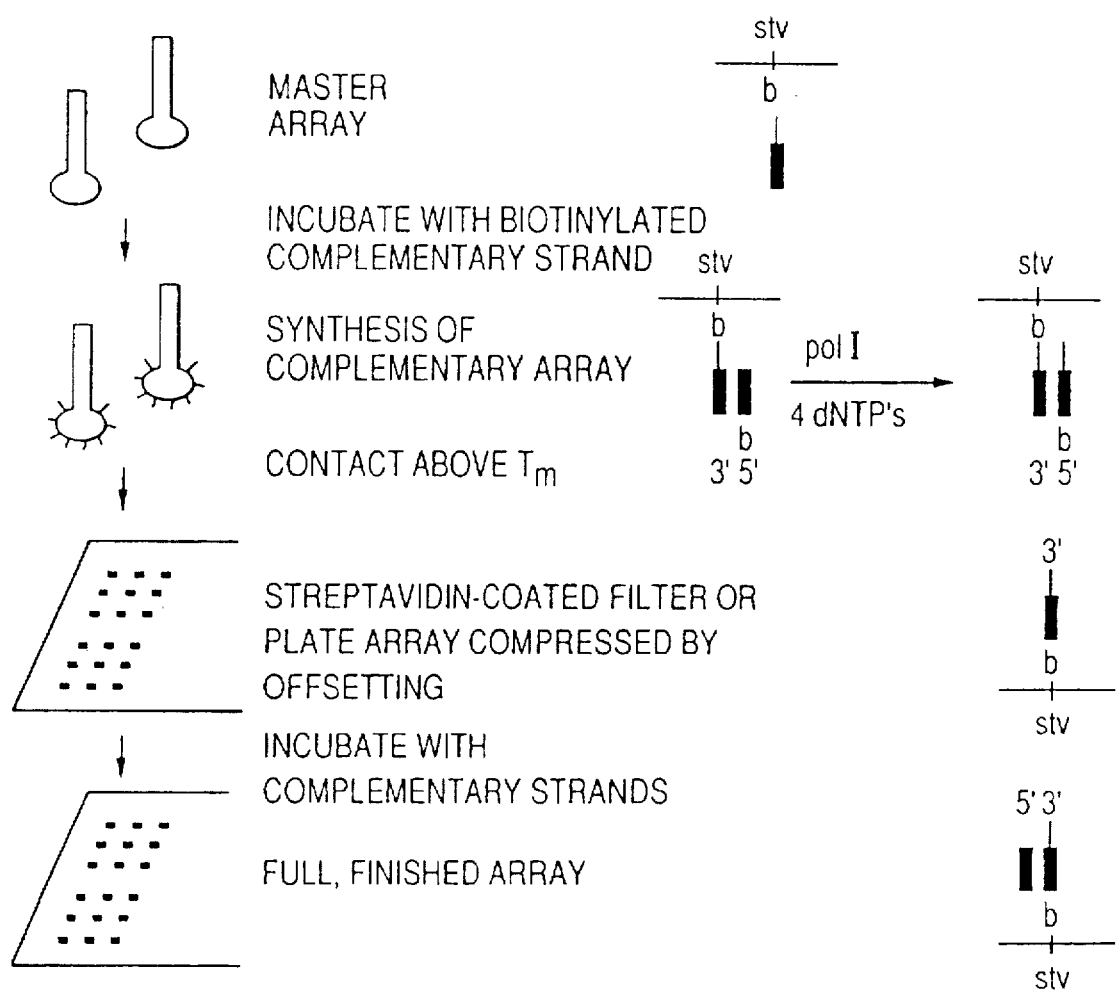
FIG. 14 A diagrammatic representation of the construction of a complimentary array of master beads.

Lastly, a rapid and highly efficient method to print arrays has been developed. Master arrays are made which direct the preparation of replicas, or appropriate complementary arrays. A master array is made manually (or by a very accurate robot) by sampling a set of custom DNA sequences in the desired pattern and then transferring these sequences to the replica. The master array is just a set of all 1024–4096 compounds. It is printed by multiple headed pipettes and compressed by offsetting. A potentially more elegant approach is shown in FIG. 14. A master array is made and used to transfer components of the replicas in a sequence-specific way. The sequences to be transferred are designed so that they contain the desired 5 or 6 base 5' variable overhang adjacent to a unique 15 base DNA sequence.

The master array consists of a set of streptavidin bead-impregnated plastic coated metal pins, each of which, at its tip, contains immobilized biotinylated DNA strands that consist of the variable 5 or 6 base segment plus the constant 15 base segment. Any unoccupied sites on this surface are filled with excess free biotin. To produce a replica chip, the master array is incubated with the complement of the 15 base constant sequence, 5' -labeled with biotin. Next, DNA polymerase is used to synthesize the complement of the 5 or 6 base variable sequence. Then the wet pin array is touched to the streptavidin-coated surface of the replica, held at a temperature above the $T_m$ of the complexes on the master array. If there is insufficient liquid carryover from the pin array for efficient sample transfer, the replica array could first be coated with spaced droplets of solvent (either held in concave cavities, or delivered by a multiheaded pipettor). After the transfer, the replica chip is incubated with the complement of 15 base constant sequence to reform the double-stranded portions of the array. The basic advantage of this scheme, if it can be realized, is that the master array and transfer compounds are made only once, and then the manufacture of replica arrays should be able to proceed almost endlessly.

Example 5

Figure 3A:
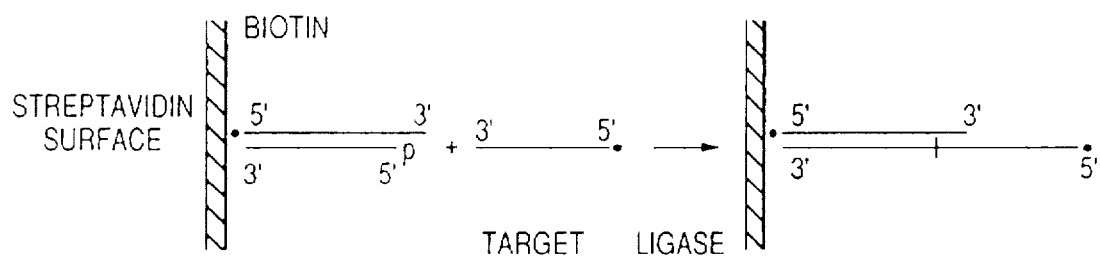
FIG. 3 Graphic representation of the ligation step of positional sequencing by hybridization wherein hybridization of the target nucleic acid produces (A) a 5' overhang or (B) a 3' overhang.

DNA ligation to oligonucleotide arrays. Following the schemes shown in FIGS. 3A and 3B, *E. coli* and T4 DNA ligases can be used to covalently attach hybridized target nucleic acid to the correct immobilized oligonucleotide probe. This is a highly accurate and efficient process. Because ligase absolutely requires a correctly base paired 3' terminus, ligase will read only the 3'-terminal sequence of the target nucleic acid. After ligation, the resulting duplex will be 23 base pairs long and it will be possible to remove unhybridized, unligated target nucleic acid using fairly stringent washing conditions. Appropriately chosen positive and negative controls demonstrate the power of this scheme, such as arrays which are lacking a 5'-terminal phosphate adjacent to the 3' overhang since these probes will not ligate to the target nucleic acid.

Figure 3B:
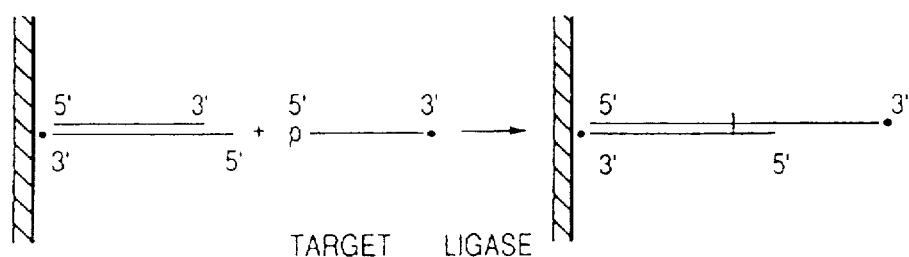
Figure 4:
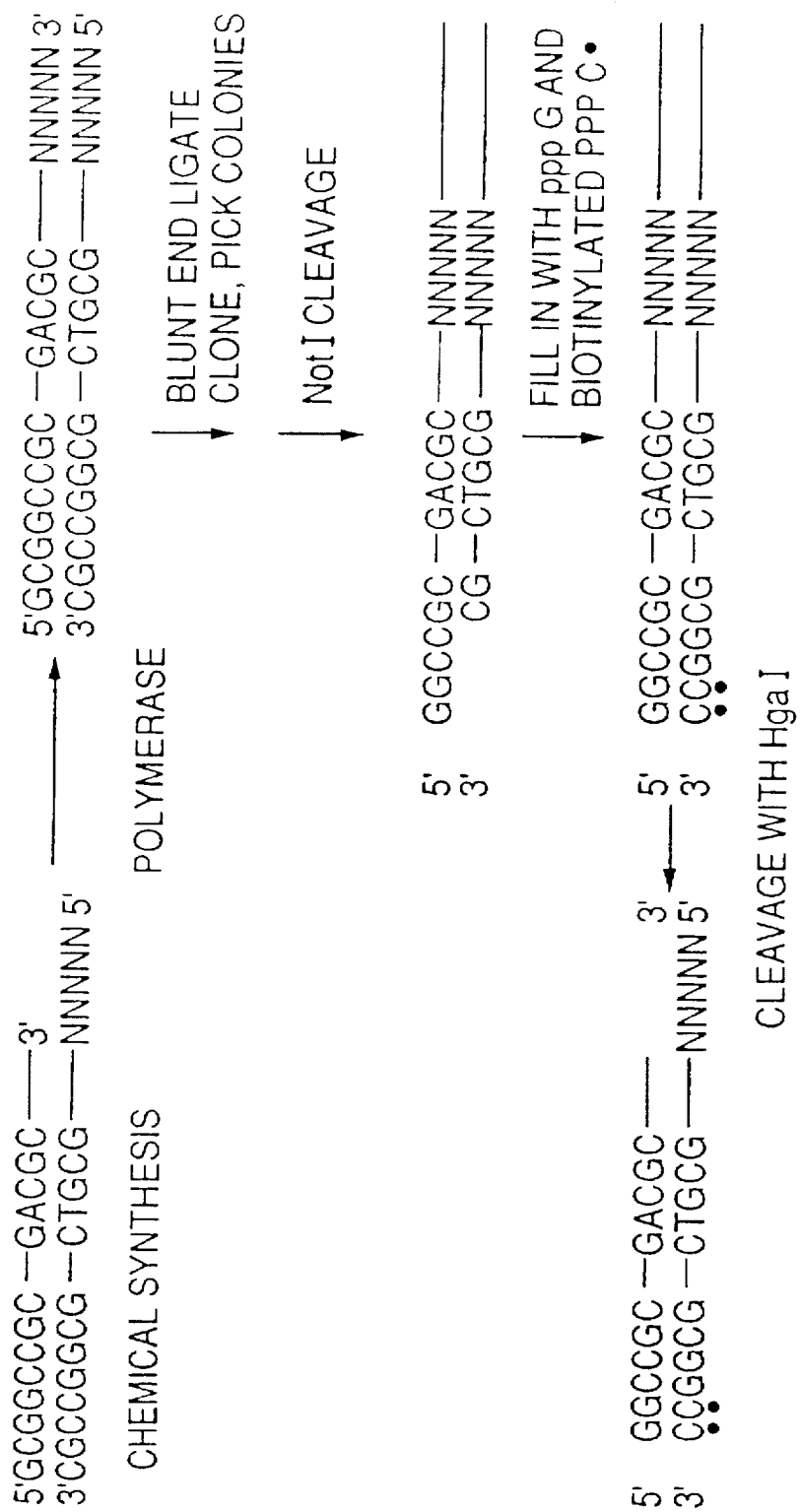
FIG. 4 Preparation of a random probe array.

There are a number of advantages to a ligation step. Physical specificity is supplanted by enzymatic specificity. Focusing on the 3' end of the target nucleic also minimize problems arising from stable secondary structures in the target DNA. As shown in FIG. 3B, ligation can be used to enhance the fidelity of detecting the 5'-terminal sequence of a target DNA.

Figure 13:
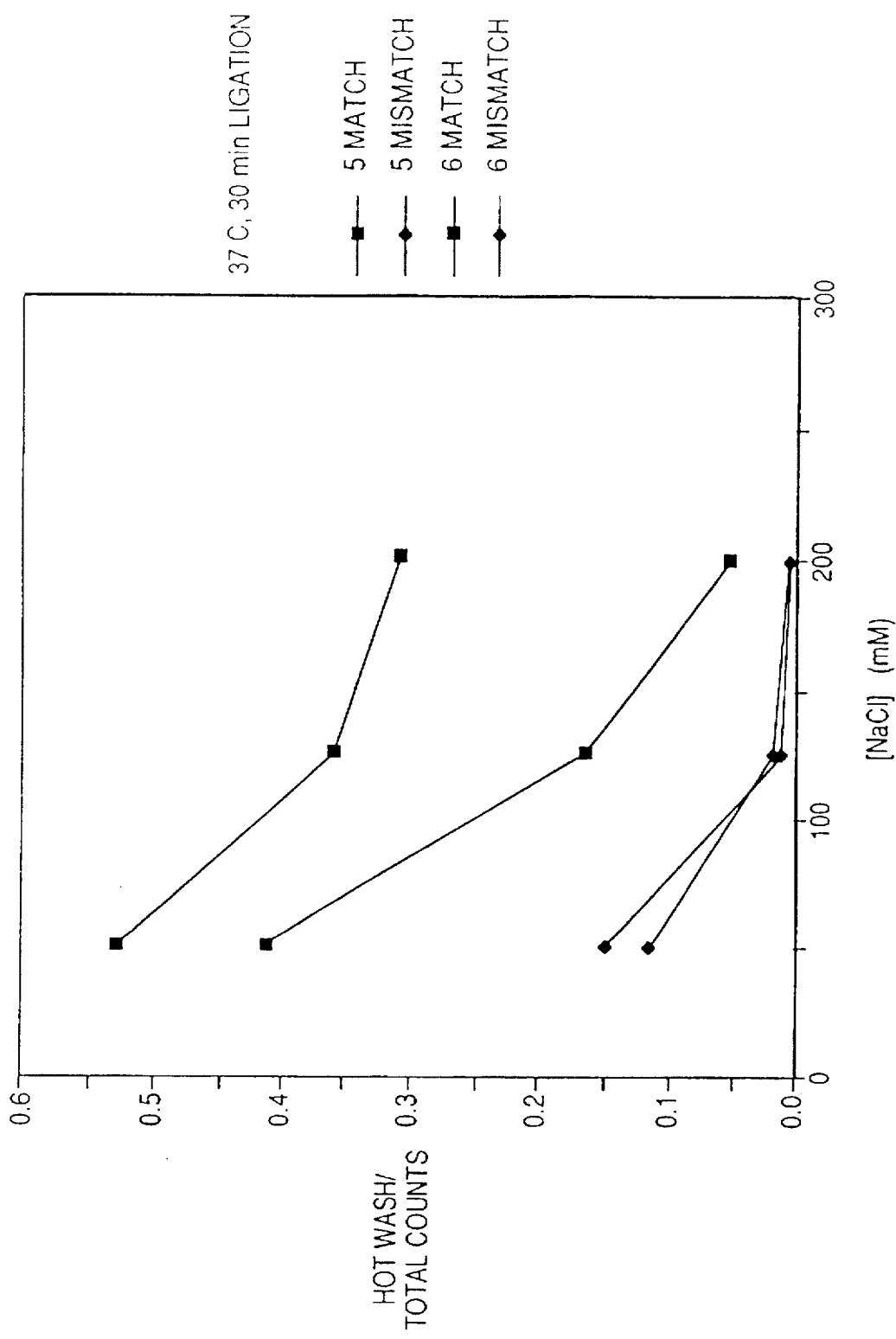
FIG. 13 Graphical representation of the ligation efficiency of positional sequencing. Depicted is the relationship between the amount of label remaining over the total amounts of label in the reaction, verses NaCl concentration.

DNA ligases are also used to covalently attach hybridized target DNA to the correct immobilized oligonucleotide probe. Several tests of the feasibility of the ligation scheme shown in FIG. 3. Biotinylated probes were attached to streptavidin-coated magnetic microbeads, and annealed with a shorter, complementary, constant sequence to produce duplexes with 5 or 6 base single-stranded overhangs. One set of actual sequences used is shown in Example 14. $^{32}$P-end labeled targets were allowed to hybridize to the Probes. Free targets were removed by capturing the beads with a magnetic separator. DNA ligase was added and ligation was allowed to proceed at various salt concentrations. The samples were washed at room temperature, again manipulating the immobilized compounds with a magnetic separator. This should remove non-ligated material. Finally, samples were incubated at a temperature above the $T_m$ of the duplexes, and eluted single strand was retained after the remainder of the samples were removed by magnetic separation. The eluate at this point should consist of the ligated material. The fraction of ligation was estimated as the amount of $^{32}$p recovered in the high temperature wash versus the amount recovered in both the high and low temperature washes. Results obtained are shown in FIG. 13. It is apparent that salt conditions can be found where the legation proceeds efficiently with perfectly matched 5 or 6 base overhangs, but not with G-T mismatches.

The results of a more extensive set of similar experiments are shown in Tables 2–4. Table 2 looks at the effect of the position of the mismatch and Table 3 examines the effect of base composition on the relative discrimination of perfect matches verses weakly destabilizing mismatches. These data demonstrate that: (1) effective discrimination between perfect matches and single mismatches occurs with all five base overhangs tested; (2) there is little if any effect of base composition on the amount of ligation seen or the effectiveness of match/mismatch discrimination. Thus, the serious problems of dealing with base composition effects on stability seen in ordinary SBH do not appear to be a problem for positional SBH; and (3) the worst mismatch positionis, as expected, the one distal from the phosphodiester bond formed in the ligation reaction. However, any mismatches that survive in this position will be eliminatd by a polymerase extension reaction, such as as described herein, provided that polymerase is used, like sequenase version 2, that has no 3'-endonuclease activity or terminal transferase activity; and (4) gel electrophoresis analysis has confirmed that the putative ligation products seen in these tests are indeed the actual products synthesized.

TABLE 3-continued

Ligation Efficiency of Matched and Mismatched Duplexes
in 0.2 M NaCl at 37° C. and
its Dependance on AT Content of the Overhang

| Overhang Sequences | | AT Content | Ligation Efficiency |
|---|---|---|---|
| Mismatch | AGCTC | | 0.02 |
| Match | AGCTC | 2/5 | 0.17 |
| Mismatch | AGCTT | | 0.01 |
| Match | AGATC | 3/5 | 0.24 |
| Mismatch | AGATT | | 0.01 |
| Match | ATATC | 4/5 | 0.17 |
| Mismatch | ATATT | | 0.01 |
| Match | ATATT | 5/5 | 0.31 |
| Mismatch | ATATC | | 0.02 |

TABLE 2

Ligation Efficiency of Matched and Mismatched Duplexes
in 0.2 M NaCl at 37° C.
(SEQ ID NO 1) 3'-TCG AGA ACC TTG GCT-5'

| | | Ligation Efficiency | |
|---|---|---|---|
| | CTA CTA GGC TGC GTA GTC-5' | | (SEQ ID NO 2) |
| 5'-B- | GAT GAT CCG ACG CAT CAG AGC TC | 0.170 | (SEQ ID NO 3) |
| 5'-B- | GAT GAT CCG ACG CAT CAG AGC TT | 0.006 | (SEQ ID NO 4) |
| 5'-B- | GAT GAT CCG ACG CAT CAG AGC TA | 0.006 | (SEQ ID NO 5) |
| 5'-B- | GAT GAT CCG ACG CAT CAG AGC CC | 0.002 | (SEQ ID NO 6) |
| 5'-B- | GAT GAT CCG ACG CAT CAG AGT TC | 0.004 | (SEQ ID NO 7) |
| 5'-B- | GAT GAT CCG ACG CAT CAG AAC TC | 0.001 | (SEQ ID NO 8) |

TABLE 3

Ligation Efficiency of Matched and Mismatched Duplexes
in 0.2 M NaCl at 37° C. and
its Dependance on AT Content of the Overhang

| Overhang Sequences | | AT Content | Ligation Efficiency |
|---|---|---|---|
| Match | GGCCC | 0/5 | 0.30 |
| Mismatch | GGCCT | | 0.03 |
| Match | AGCCC | 1/5 | 0.36 |

TABLE 4

Increasing Discrimination by Sequencing Extension at 37° C.

| | | Ligation Efficiency (percent) | Ligation Extension (cpm) | |
|---|---|---|---|---|
| | | | (+) | (−) |
| | (SEQ ID NO 1) 3'-TCG AGA ACC TTG GCT-5'* CTA CTA GGC TGC GTA GTC-5'(SEQ ID NO 2) | | | |
| 5'-B- | GAT GAT CCG ACG CAT CAG AGA TC (SEQ ID NO 9) | 0.24 | 4,934 | 29,500 |
| 5'-B- | GAT GAT CCG ACG CAT CAG AGC TT (SEQ ID NO 10) | 0.01 | 116 | 250 |
| | Discrimination = (SEQ ID NO 1) 3'-TCG AGA ACC TTG GCT-5'* CTA CTA GGC TGC GTA GTC-5'(SEQ ID NO 2) | ×24 | ×42 | ×118 |
| 5'-B- | GAT GAT CCG ACG CAT CAG ATA TC (SEQ ID NO 11) | 0.17 | 12,250 | 25,200 |

TABLE 4-continued

Increasing Discrimination by Sequencing Extension at 37° C.

|  | Ligation Efficiency (percent) | Ligation Extension (cpm) (+) | Ligation Extension (cpm) (−) |
|---|---|---|---|
| 5'-B- GAT GAT CCG ACG CAT CAG ATA TT (SEQ ID NO 12) | 0.01 | 240 | 390 |
| Discrimination = | ×17 | ×51 | ×65 |

"B" = Biotin
"*" = radioactive label

The discrimination for the correct sequence is not as great with an external mismatch (which would be the most difficult case to discriminate) as with an internal mismatch (Table 4). A mismatch right at the ligation point would presumably offer the highest possible discrimination. In any event, the results shown are very promising. Already there is a level of discrimination with only 5 or 6 bases of overlap that is better than the discrimination seen in conventional SBH with 8 base overlaps. Allele-specific amplification by the ligase chain reaction also appears to be quite successful (F. Baranay et al., Proc. Natl. Acad. Sci. USA 88:189–93, 1991).

Example 6

Figure 6:
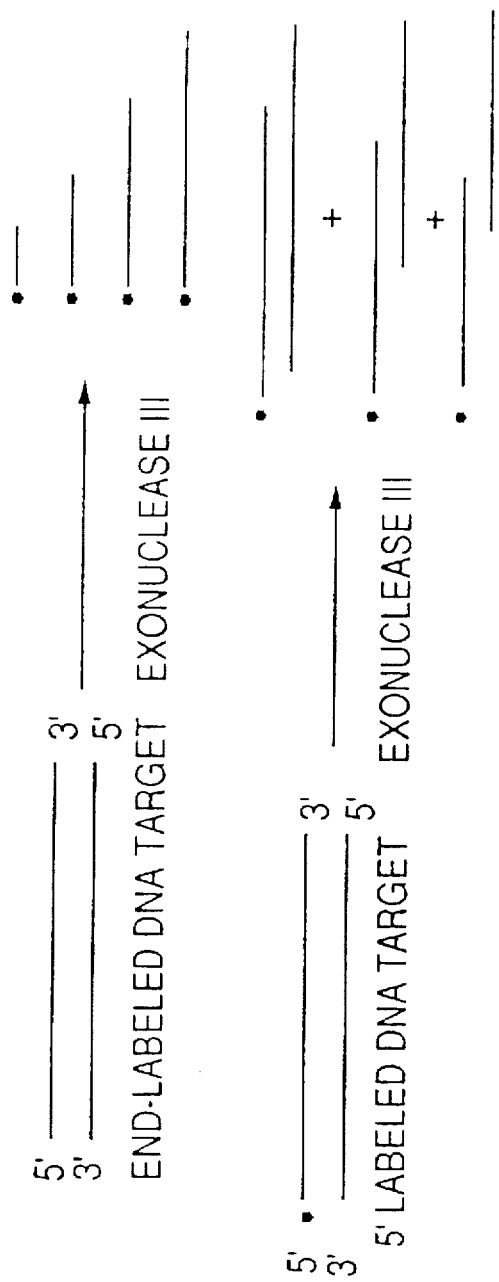
FIG. 6 Preparation of a nested set of targets using labeled target nucleic acids partially digested with exonuclease III.

Positional sequencing by hybridization with a nested set of DNA samples. Thus far described arrays have been very inefficiently utilized because with only a single target nucleic acid, only a single probe will be detected. This clearly wastes most of the potential information intrinsically available from the array. A variation in the procedures will use the array much more efficiently. This is illustrated in FIG. 6. Here, before hybridization to the probe array, the 5'-labeled (or unlabeled) target nucleic acid is partially degraded with an enzyme such as exonuclease III. Digestion produces a large number of molecules with a range of chain lengths that share a common 5'-terminus, but have a variable 3'-terminus. This entire family of nucleic acids is then hybridized to the probe array. Assuming that the distribution of 3'-ends is sufficiently broad, the hybridization pattern should allow the sequence of the entire target to be read subject to any branch point ambiguities. If a single set of exonuclease conditions fails to provide a broad enough distribution, samples could be combined and prepared under several different conditions.

There are at least three ways to make nested DNA deletions suitable for positional SBH. The easiest, but ultimately probably the least satisfactory, is to use exonuclease like exonuclease III, by analogy to nested deletion cloning in ordinary sequencing (S. Henikoff, Gene 28:351–58, 1984). The difficulty with these enzymes is that they may not produce an even enough yield of compounds to fully represent the sample of interest. One sees a pattern of regions in the sequence where the enzyme moves relatively rapidly, and others where it moves relatively slowly. Several commercially available enzymes can be examined by looking at the distribution of fragment lengths directly on ordinary polyacrylamide DNA sequencing gels.

The second approach to making nested samples is to use the ordinary Maxam-Gilbert sequencing chemistry. It is possible to ligate the 5'-phosphorylated fragments which result from these chemical degradations. Indeed this is the principle use for ligation-mediated genomic DNA sequencing (G. P. Pfiefer et al., Sci. 246:810–13, 1989). Asymmetric PCR or linear amplification can be used to make the complementary, ligatable, nested strands. A side benefit of this approach is that one can pre-select which base to cleave after, and this provides additional information about the DNA sequences one is working with.

The third approach to making nested samples is to use variants on plus/minus sequencing. For example, one can make a very even DNA sequencing ladder by using Sanger sequencing with a dideoxy-pppN terminator. This does not produce a ligatable end. However it can be replaced with a ligatable end, while still on the original template, by first removing the ddpppN with the 3' editing-exonuclease activity of DNA polymerase I in the absence of the one particular base at the end. Note that this accomplishes two things for the price of one. Not only does it generate a ladder with a ligatable, end, because one can pre-determine the identity of the base removed, it provides an additional nucleotide of DNA sequence information. One can use single color detection in four separate reactions, or ultimately, four color detection by mixing the results of four separate reactions prior to hybridization. If this approach is successful, it is amenable to more elaborate variations combining laddering and hybridization. Note that each of these procedures combines some of the power of ladder sequencing with the parallel processing of SBH.

In addition, there are alternative methods of preparing the desired samples, such as polymerization in the absence of limiting amounts of one of the substrate bases, such as for DNA, one of the four dNTPs. Standard Sanger or Maxam-Gilbert sequencing protocols cannot be used to generate the ladder of DNA fragments because these techniques fail to yield 3'-ligatable ends. In contrast, sequencing by the method of the present invention combines the techniques and advantages of the power of ladder sequencing with the parallel processing power of positional sequencing by hybridization.

Figure 5:
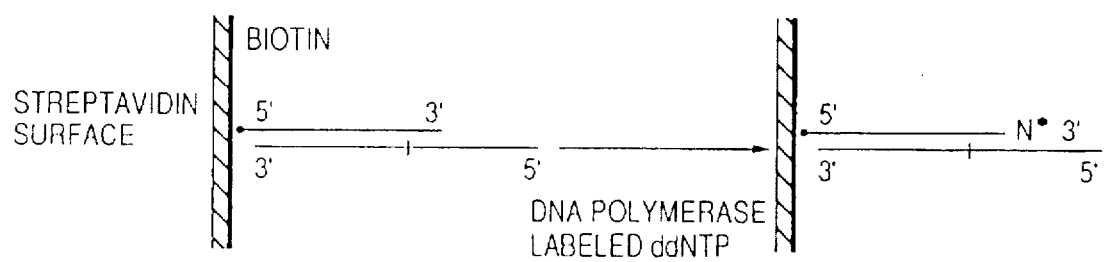
FIG. 5 Single nucleotide extension of a probe hybridized with a target nucleic acid using DNA polymerase and a single dideoxynucleotide.

Ligation ensures the fidelity of detection of the 3' terminal base of the target DNA. To ensure similar fidelity of detection at the 5' end of the duplex formed between the probe and the target, the probe-target duplex can be extended after ligation by one nucleotide using, for example, a labeled ddNTP (FIG. 5). This has two major advantages. First, specificity is increased because extension with the Klenow fragment of DNA polymerase requires a correctly base paired 3'-primer terminus. Second, using labeled ddNTPs one at a time, or a mixture of all four labeled with four different colors simultaneously, the identity of one additional nucleotide of the target nucleic acid can be determined as shown in FIG. 5. Thus, an array of only 1024 probes would actually have the sequencing power of an array of 4096 hexamers, in other words, a corresponding four-fold gain for any length used. In addition, polymerases work well in solid state sequencing methodologies quite analogous of the type proposed herein.

Example 7

Retaining positional information in sequencing by hybridization. Inherent in the detection of just the 3'-terminal sequence of the target nucleic acid, is the possibility of obtaining information about the distance between the sequence hybridized and a known reference point. Although that point could be arbitrary, the 5'-end of the intact target was used. The desired distance is then just the length of the DNA fragment that has hybridized to a particular probe in the array. In principle, there are two ways to determine this length. One is to length fractionate (5' labeled) DNA before or after the hybridization, ligation, and any DNA polymerase extension. Single DNA sequences could be used, but pools of many DNA targets used simultaneously or, alternatively, a double-labeled target with one color representing the 5'-end of any unique site and the other a random internal label would be more efficient. For example, incorporated into the target is a fractional amount, for example, about 1%, of biotinylated (or digoxigenin-labeled) pyrimidines, and use this later on for fluorescent detection. It has been recently shown that an internal label is effective in high sensitivity conventional ladder DNA sequencing. The ratio of the internal label to the end label is proportional to target fragment length. For any particular sample the relationship is monotonic even though it may be irregular. Thus, correct order is always obtained even if distances are occasionally distorted by extreme runs of purines of pyrimidines. If necessary, it is also possible to use two quasi-independent internal labeling schemes.

The scheme as just outlined, used with polymerase extension, might require as many as 6 different colored labels; 2 on the target (5' and internal) and four on the probe extension (four ddNTPs). However the 5' label is unnecessary, since the 3' extension provides the same information (providing that the DNA polymerase reaction is close to stoichiometric). The ddNTPs can be used one at a time if necessary. Therefore, the scheme could proceed with as little as two color detection, if necessary (FIG. 7), and three colors would certainly suffice.

Figure 7:
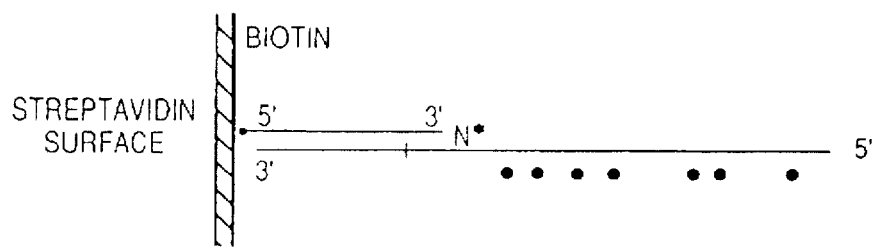
FIG. 7 Determination of positional information using the ratio of internal label to terminal label.

A scheme complimentary to that shown in FIG. 7 would retain positional information while reading the 5'-terminal sequence of 3'-end labeled plus internally labeled target nucleic acids. Here, as in FIG. 3B, probe arrays with 5' overhangs are used, however, polymerase extension will not be possible.

Example 8

Resolution of branch point ambiguities. In current SBH, branch point ambiguities caused by sequence recurrences effectively limit the size of the target DNA to a few hundred base pairs. The positional information described in Section 6 will resolve many of these ambiguities. When a sequence recurrence occurs, if a complete DNA ladder is used as the sample, two or more targets will hybridize to the same probe. Single nucleotide additions will be informative in ¾ of the cases where two targets are ligated to the same probe; they will reveal that a given probe contains two different targets and will indicate the sequence of one base outside the recurrence. The easiest way to position the two recurrent sequences is to eliminate the longer or shorter members of the DNA ladder and hybridize remaining species to the probe array. This is a sufficiently powerful approach that it is likely to be a routine feature of positional SBH. Recurrences will be very frequent with only 5 or 6 base overhangs, but the use of segmented ladders will allow most of these to be resolved in a straightforward way. It should not be necessary to physically fractionate the DNA species of the ladder (although this could certainly be done if needed). Instead, one can cut an end-labeled ladder with a restriction nuclease. For an effective strategy seven 4-base specific enzymes should be used, singly or in combination.

Additional information is available for the recurrence of pentanucleotide sequences by the use of polymerase and single base extension as described in Example 7. In three cases out of four the single additional base will be different for the two recurrent sequences. Thus, it will be clear that a recurrence has occurred.

The real power of the positional information comes, not from its application to the recurrent sequences, but to its applications to surrounding unique sequences. Their order will be determined unequivocally, assuming even moderately accurate position information, and thus, the effect of the branch point will be eliminated. For example, 10% accuracy in intensity rations for a dual labeled 200 base pair target will provide a positional accuracy of 20 base pair. This would presumably be sufficient to resolve all but the most extraordinary recurrences.

Branch point ambiguities are caused by sequence recurrence and effectively limit the size of the target nucleic acid to a few hundred base pairs. However, positional information derived from Example 7 will resolve almost all of these ambiguities. If a sequence recurs, more than one target fragment will hybridize to, or otherwise be detected by subsequent ligation to or extension from a single immobilized probe. The apparent position of the target will be its average on the recurrent sequence. For a sequence which occurs just twice, the true location is symmetric around the apparent one. For example, the apparent position of a recurrent sequence occurring in positions 50 and 100 bases from the 5'-end of the target will be 75 bases from the end. However, when the pattern of positional sequencing by hybridization is examined, a sequence putatively located at that position will show overlap with contacts in the neighborhood of 50 bases and 100 bases from the 5'-end. This will indicate that a repeat has occurred.

Example 9

Figure 8:
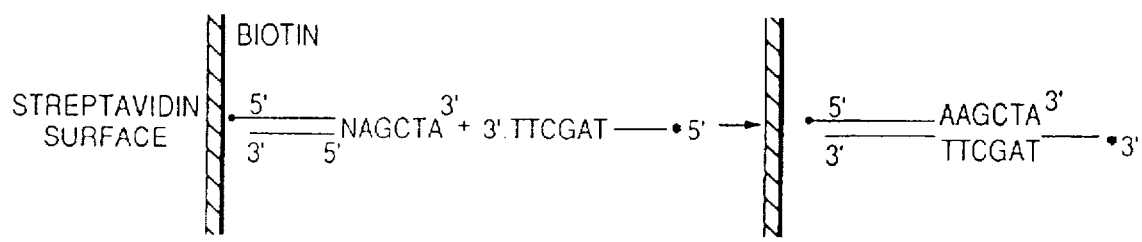
FIG. 8 (A) Extension of one strand of the probe using a hybridized target as template with a single deoxynucleotide.
(B) Hybridization of target with a fixed probe followed by ligation of probe to target.
Figure 10:
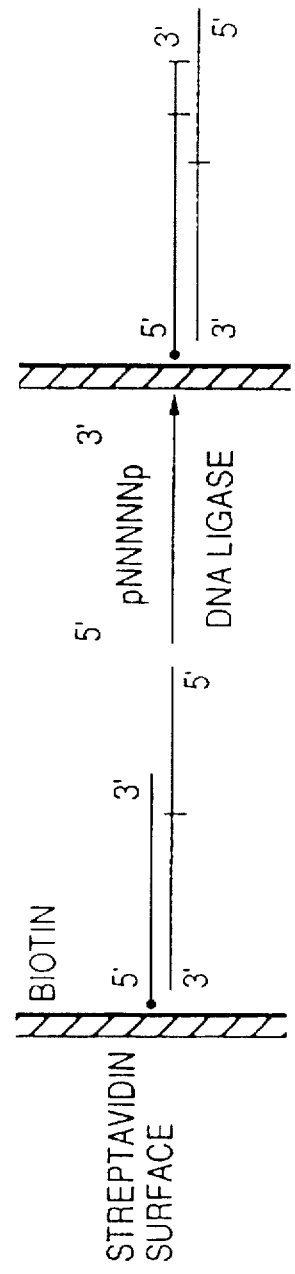
FIG. 10 Extension of a nucleic acid probe by ligation of a pentanucleotide 3' blocked to prevent polymerization.

Extending the 3'-sequence of the target. Using the scheme shown in FIG. 8, it is possible to learn the identity of the base 3' to the known sequence of the target, as revealed by its hybridization position on an oligonucleotide array. For example, an array of $4^n$ single-stranded overhangs of the type NAGCTA 3', as shown in the Figure, are created wherein n is the number of known bases in an overhang of length n+1. The target is prepared by using a 5' label in the manner shown in FIG. 3. The Klenow fragment of DNA polymerase would then be used to add a single dpppNp as a polymerization chain terminator (or alternatively, ddpppN terminators plus ligatable ends). Before hybridization the resulting 3'-terminal phosphate would be removed by alkaline phosphatase. This would allow subsequent ligation of the target to the probe array. Either by four successive single color 5' labels, or a mixture of four different colored chains, each color corresponding to a particular chain terminator, one would be able to infer the identity of the base that had paired with the N next to the sequence AGCTA. Labeling of the 5' end minimizes interference of fluorescent base derivatives on the ligation step. Presumably, provided with a supply of dpppNp, or ribo-pppNp which can be easily prepared, the sequenase version 2 or another known polymerase will use these as a substrate. The key step in this scheme is to add a single dpppNp as a polymerization chain terminator. Before hybridization, the resulting 3' terminal phosphate is removed by alkaline phosphatase. This allows for the subsequent ligation of the target to the probe array. Alternatively, ddpppNp terminators replaced with ligatable ends may also be used. Either by four successive single color 5' labels, or a mixture of four different colored chains, each color representing a specific chain terminator, one is able to infer the identity of the base that had paired with the N next to the sequence AGCTA. The 5' end is labeled to minimize interference of fluorescent-based derivatives with the ligation step.

Assuming that there are sufficient colors in a polychromatic detection scheme, this 3' target extension can be combined with the 3' probe extension to read n+2 bases in an array of complexity $4^n$. This is potentially quite a substantial improvement. It decreases the size of the array needed by a factor of 16 without any loss in sequencing power. However, the number of colors required begins to become somewhat daunting. In principle one would want at least nine, four for each 3' extension and one general internal label for target length. However, with resonance ionization spectroscopy (RIS) detection, eight colors are available with just a single type of metal atom, and many more could be had with just two metals.

Example 10

Extending the 5' sequence of the target. In example 5, it was illustrated that by polymerase extension of the 3'-end of the probe, a single additional nucleotide on the target could be determined after ligation. That procedure used only chain terminators. Florescent labeled dNTPs that serve as substrates for DNA polymerase and other enzymes of DNA metabolism can also be made. The probe-target complex of each ligation reaction with, for example, three labeled dNTPs and a fourth unlabeled chain terminator could be extended using fluorescent labeled dNTPs. This could be repeated, successively, with each possible chain terminator. If the ratio of the intensities of the different labels can be measured fairly accurately, a considerable amount of additional sequence information will be obtained. If the absolute intensities could be measured, the power of the method appears to be very substantial since one is in essence doing a bit of four color DNA sequencing at each site on the oligonucleotide array. For example, as shown in FIG. 9, for the sequence (Pu)$_4$T, such an approach would unambiguously reveal 12 out of the 16 possible sequences and the remainder would be divided into two ambiguous pairs each. Alternatively, once the probe array has captured target DNAs, full plus-minus DNA sequencing reactions could be carried out on all targets. Single nucleotide DNA addition methods have been described that would also be suitable for such a highly parallelized implementation.

Example 11

Sample pooling in positional sequencing by hybridization. A typical 200 base pair target will detect only 196 probes on a five base 1024 probe array. This is not far from the ideal case in single, monochromatic sampling where one might like to detect half the probes each time. However, as the procedure is not restricted to single colors, the array is not necessarily this small. With an octanucleotide array, in conventional positional sequencing by hybridization or one of its herein described enhancements, the target detects only $\frac{1}{32}$ of the immobilized probes. To increase efficiency a mixture of 16 targets can be used with two enhancements. First, intelligently constructed orthogonal pools of probes can be used for mapping by hybridization. Hybridization sequencing with these pools would be straightforward. Pools of targets, pools of probes, or pools of both can be used.

Second, in the analysis by conventional sequencing by hybridization of an array of $2 \times 10^4$ probes, divided into as few as 24 pools containing $8 \times 10^3$ probes each, there is a great deal of redundancy. Excluding branch points, 24 hybridizations could determine all the nucleic acid sequences of all the targets. However, using RIS detection there are much more than 24 colors. Therefore, all the hybridizations plus appropriate controls could be done simultaneously, provided that the density of the nucleic acid sample were high enough to keep target concentration far in excess of all the probes. A single hybridization experiment could produce $4 \times 10^6$ base pairs of sequence information. An efficient laboratory could perform 25 such hybridizations in a day, resulting in a throughput of $10^8$ base-pairs of sequence per day. This is comparable to the speed of polymerization by *E. coli* DNA polymerase.

Example 12

Oligonucleotide ligation after target hybridization. Stacking hybridization without ligation has been demonstrated in a simple format. Eight-mer oligonucleotides were annealed to a target and then annealed to an adjacent 5-mer to extend the readable sequence from 8 to 13 bases. This is done with small pools of 5-mers specifically chosen to resolve ambiguities in sequence data that has already been determined by ordinary sequencing by hybridization using 8-mers alone. The method appears to work quite well, but it is cumbersome because a custom pool of 5-mers must be created to deal with each particular situation. In contrast, the approach taken herein (FIG. 9), after ligation of the target to the probe, is to ligate a mixtures of 5-mers arranged in polychromatically labeled orthogonal pools. For example, using 5-mers of the form pATGCAp or pATGCddA, only a single ligation event will occur with each probe-target complex. These would be 3' labeled to avoid interference with the ligase. Only ten pools are required for a binary sieve analysis of 5-mers. In reality it would make sense to use many more, say 16, to introduce redundancy. If only four colors are available, those would require four successive hybridizations. For example, sixteen colors would allow a single hybridization. But the result of this scheme is that one reads ten bases per site in the array, equivalent to the use of $4^{10}$ probes, but one only has to make $2 \times 4^5$ probes. The gain in efficiency in this scheme is a factor of 500 over conventional sequencing by hybridization.

Example 13

Synthesis of custom arrays of probes. Custom arrays of probe would be useful to detect a change in nucleic acid sequence, such as any single base change in a pre-selected large population of sequences. This is important for detecting mutations, for comparative sequencing, and for finding new, potentially rare polymorphisms. One set of target sequences can be customized to an initial general array of nucleic acid probes to turn the probe into a specific detector for any alterations of a particular sequence or series of sequences. The initial experiment is the same as outlined above in Example 4, except that the 3'-blocked 5-mers are unlabeled. After the ligation, the initial nucleic acid target strand along with its attached 18 nucleotide stalk is removed, and a new unligated 18 nucleotide stalk annealed to each element of the immobilized array (FIG. 11). The difference is that because of its history, many (ideally 50% or more), of the elements of that array now have 10 base 3' extensions instead of 5 base extensions. These do not represent all $4^{10}$ possible 10-mers, but instead represent just those 10-mers which were present in the original sample. A comparison sample can now be hybridized to the new array under conditions that detect single mismatches in a decanucleotide duplex. Any samples which fail to hybridize are suspects for altered bases.

A problem in large scale diagnostic DNA sequencing is handling large numbers of samples from patients. Using the approach just outlined, a third or a fourth cycle of oligonucleotide ligation could be accomplished creating an array of 20-mers specific for the target sample. Such arrays would be capable of picking up unique segments of genomic DNA in a sequence specific fashion and detecting any differences in them in sample comparisons. Each array could be custom designed for one individual, without any DNA sequence determination and without any new oligonucleotide synthesis. Any subsequent changes in that individual's DNA such as caused by oncogenesis or environmental insult, might be easily detectable.

Example 14

Positional sequencing by hybridization. Hybridization was performed using probes with five and six base pair overhangs, including a five base pair match, a five base pair mismatch, a six base pair match, and a six base pair mismatch. These sequences are depicted in Table 5.

TABLE 5

Test Sequences:

5 bp overlap, perfect match:

| | |
|---|---|
| 5'-TCG AGA ACC TTG GCT*-3' | (SEQ ID NO 1) |
| 3'-CTA CTA GGC TGC GTA GTC | (SEQ ID NO 2) |
| 5'-biotin-GAT GAT CCG ACG CAT CAG AGC TC-3' | (SEQ ID NO 3) |

5 bp overlap, mismatch at 3' end:

| | |
|---|---|
| 5'-TCG AGA ACC TTG GCT*-3' | (SEQ ID NO 1) |
| 3'-CTA CTA GGC TGC GTA GTC | (SEQ ID NO 2) |
| 5'-biotin-GAT GAT CCG ACG CAT CAG AGC TT-3' | (SEQ ID NO 4) |

6 bp overlap, perferct match:

| | |
|---|---|
| 5'-TCG AGA ACC TTG GCT*-3' | (SEQ ID NO 1) |
| 3'-CTA CTA GGC TGC GTA GTC | (SEQ ID NO 2) |
| 5'-biotin-GAT GAT CCG ACG CAT CAG AGC TCT-3' | (SEQ ID NO 13) |

6 bp overlap, mismatch four bases from 3' end:

| | |
|---|---|
| 5'-TCG AGA ACC TTG GCT*-3' | (SEQ ID NO 1) |
| 3'-CTA CTA GGC TGC GTA GTC | (SEQ ID NO 2) |
| 5'-biotin-GAT GAT CCG ACG CAT CAG AGT TCT-3' | (SEQ ID NO 14) |

Figure 12:
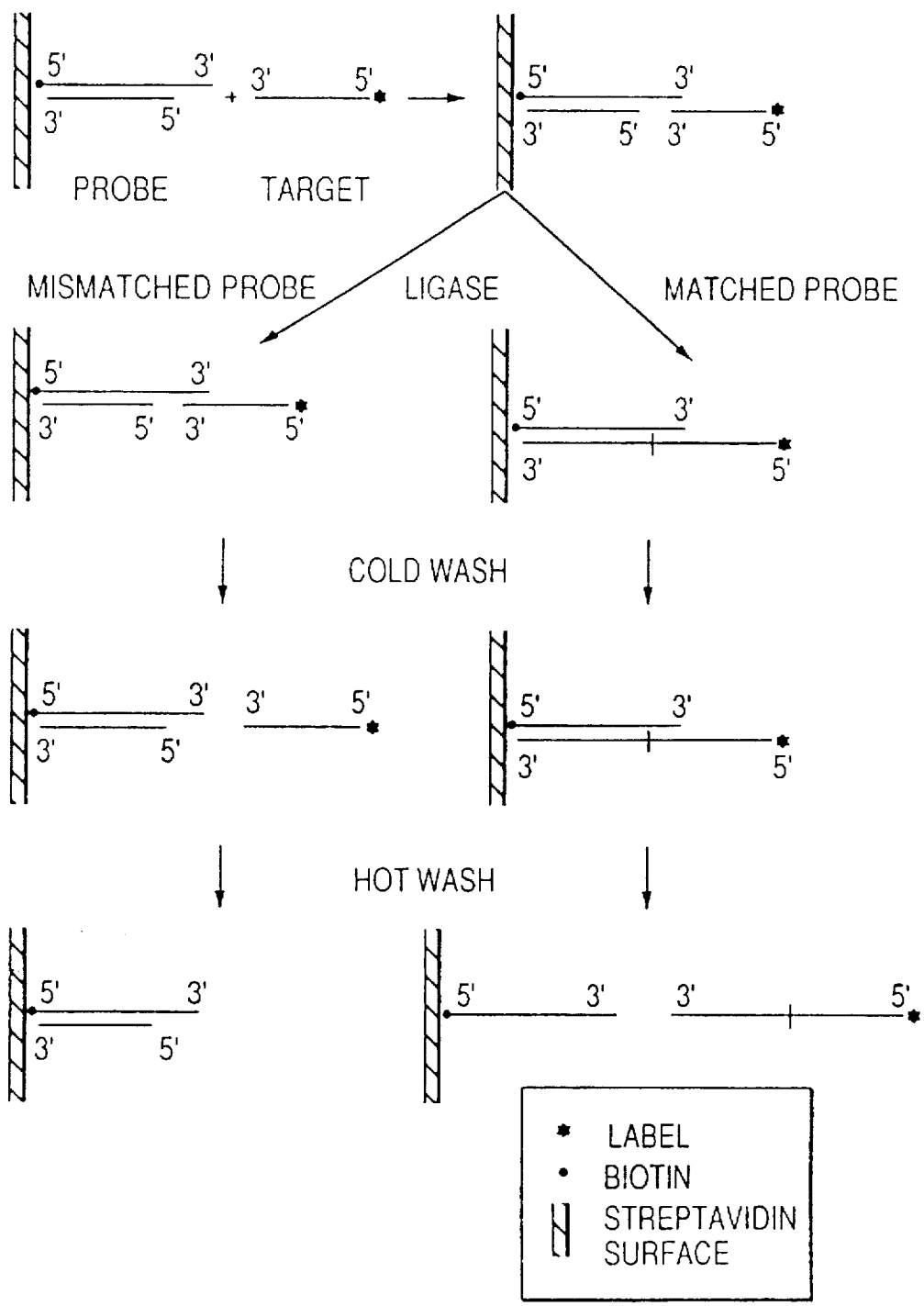
FIG. 12 Graphic representation of the general procedure of positional sequencing by hybridization.

The biotinylated double-stranded probe was prepared in TE buffer by annealing the complimentary single strands together at 68° C. for five minutes followed by slow cooling to room temperature. A five-fold excess of monodisperse, polystyrene-coated magnetic beads (Dynal) coated with streptavidin was added to the double-stranded probe, which as then incubated with agitation at room temperature for 30 minutes. After ligation, the samples were subjected to two cold (4° C.) washes followed by one hot (90° C.) wash in TE buffer (FIG. 12). The ratio of $^{32}$P in the hot supernatant to the total amount of $^{32}$P was determined (FIG. 13). At high NaCl concentrations, mismatched target sequences were either not annealed or were removed in the cold washes. Under the same conditions, the matched target sequences were annealed and ligated to the probe. The final hot wash removed the non-biotinylated probe oligonucleotide. This oligonucleotide contained the labeled target if the target had been ligated to the probe.

Example 15

Compensating for variations in base composition. A major problem in all suggested implementations of SBH is the rather marked dependence of $T_m$ on base composition, and, at least in some cases, on base sequence. The use of unusual salts like tetramethyl ammonium halides or betaines (W. A. Rees et al., Biochemistry 32:137–44, 1993) offers one approach to minimizing these varieties. Alternatively, base analogs like 2,6-diamino purine and 5-bromo U can be used instead of A and T, respectively to increase the stability of A-T base paris, and derivatives like 7-deazaG can be used to decrease the stability of G-C base pairs. The initial experiments shown in Table 2 indicate that the use of enzymes will eliminate many of the complications due to base sequences. This gives the approach a very significant advantage over non-enzymatic methods which require different conditions for each nucleic acid and are highly matched to GC content.

Another method to compensate for differences in stability is to vary the base next to the stacking site. Experiments are performed to test the relative effects of all four bases in this position on overall hybridization discrimination and also on relative ligation discrimination. Base analogs such as dU (deoxyuridine) and 7-deazaG are also tested as components of the target DNA to see if these can suppress effects of secondary structure. Single-stranded binding proteins may also be helpful in this regard.

Example 16

Data measurement, processing and interpretation. Highly automated methods for raw data handling and generation of contiguous DNA sequence from the hybridization are required for analysis of the data. Two methods of data acquisition have been used in prior SBH efforts. CCD cameras with fluorescent labels and image plate analyzers with radiolabeled samples. The latter method has the advantage that there is no problem with uniform sampling of the array. However it is effectively limited to only two color analysis of DNA samples, by the use of $^{35}$S and $^{32}$P, differentially imaged through copper foil. In contrast, while CCD cameras are less well developed, the detection of many colors is possible by the use of appropriate exciting sources and filters. Four colors are available with conventional fluorescent DNA sequencing primers or terminators. More than four colors may be achievable if infra-red dyes are used. However, providing uniform excitation of the fluorescent array is not a trivial problem. Both detection schemes are used and the image plate analyzers are sure to work. The CCD camera approach will be necessary if some of the multicolor labeling schemes described in the proposal are ever to be realized. Label will introduced into targets by standard enzymatic methods, such as the use of 5' labeled PCR primers, for 5' labeling, internally alpha $^{32}$P labeled triphosphates or fluorescent-labeled base analogs for internal labeling, and similar compounds by filling in staggered DNA ends for 3' labeling.

Both the Molecular Dynamics image plate analyzer and the Photometrics cooled CCD camera can deal with the same TIFF 8 bit data formate. Thus, software developed for either instrument can be used to handle data measured on both instruments. This will save a great deal of unnecessary duplication in data processing software. Sequence interpretation software can be developed for reading sequencing chip data and assembling it into contiguous sequence are already underway in Moscow, at Argonne National Laboratory, and in the private sector. Such software is generally available in the interested user community. The most useful examples of this software can be customized to fit the particularly special needs of this approach including polychromatic detection, incorporation of positional information, and pooling schemes. Specific software developments for constructing and decoding the orthogonal pools of samples that may ultimately be used are being developed because these procedures are also needed for enhanced physical mapping methods.

Example 17

Generation of master beads. The general procedure for the generation of master beads is depicted in FIG. 14. Forty microliters of Dynabeads M-280 Streptavidin were washed twice with 80 µl of TE (bead concentration of 5 mg/ml). Final concentration of beads was about 5–10 pmoles of biotinylated oligo for 40 µg of beads in a total volume of 80 µl. East test oligo, in the form 5'-biotin-$N_1$ $N_2$ $N_3$ $N_4$ $N_5$-10 bp-3', was dissolved in TE to a concentration of 10 pmol/40 µl (250 nM). Eighty microliters of oligo were added and the mixture shaken gently for 15 minutes in a vortex at low speed.

TABLE 6

| Stock solutions of MPROBEN in 1 ml Tb pH 7.5 | | | |
|---|---|---|---|
| MPROBEA | 94 µg | 12,200 pmol | 20 µl in 1 ml |
| MPROBEC | 121 µg | 15,800 pmol | 16 µl in 1 ml |
| MPROBEG | 94 µg | 12,300 pmol | 20 µl in 1 ml |
| MPROBET | 147 µg | 19,200 pmol | 13 µl in 1 ml |
| Stock solution of MCOMPBIO in 5 ml Tb pH 7.5 | | | |
| MCOMPBIO | | 464,000 pmol | 5 µl in 1.85 ml |

Tubes were placed in the Dynal MPC apparatus and the supernatant removed. Unbound streptavidin sites were sealed with 5 µl of 200 µM free biotin in water. Wash the beads several times with 80 µl TE. These beads can store in this state at 4° C. for several weeks.

250 nM of 5'-biotinylated 18 base nucleic acid (the complement of the constant region) served as primer for enzymatic extension of the probe region. The tube was heated to 68° C. and allowed to cool to room temperature. Beads were kept in suspension by tipping gently. Supernatant was removed and washed with 40 µl TE several times. The tube was removed from the magnet and the beads resuspended in 40 µl of TE to remove excess complement. The bead suspension was equally divided among 4 tubes and the stock tube washed with the wash divided among the tubes as well. Supernatant was removed and washed with water. Each tube contained about 2–5 pmol of DNA (28–72 ng; see Table 6).

Polymerase I extension was performed on each tube of DNA in a total of 13 µl as follows (see Table 7): NEB buffer concentration was 10 mM Tris-HCl, pH 7.5, 5 mM $MgCl_2$, 7.5 mM DTT; 33 µM d(N-$N_i$)TP mix; 2 µM+$^{32}$P d$N_i$TP complimentary to one of the $N_i$ bases; and polymerase I large fragment (klenow). In the first well was added dTTP, dCTP and dGTP, to a concentration of 33 µM. $^{32}$P-dATP was added to a concentration of 3 µM. dNTP stock solutions of 200 µM were pooled to lack the labelled nucleotide (i.e. Tube A contains C,G and T) adding 6.3 µl dNTP, 5 µl 200 µM dNTP, and 43 µl water. Radioactively labeled (*dNTP) stock solutions were 20 µM prepared from 2 µl |α$^{32}$P| dNTP, 5 µl 200 µM dNTP, and 43 µl water.

TABLE 7

| TUBE # | A | C | G | T |
|---|---|---|---|---|
| 10 × buffer | 1.3 µl | 1.3 µl | 1.3 µl | 1.3 µl |
| dATP | 1.5 µl* | 2.1 µl | 2.1 µl | 2.1 µl |
| dCTP | 2.1 µl | 1.5 µl* | 2.1 µl | 2.1 µl |
| dGTP | 2.1 µl | 2.1 µl | 1.5 µl* | 2.1 µl |
| dTTP | 2.1 µl | 2.1 µl | 2.1 µl | 1.5 µl* |
| Enzyme | 1 µl | 1 µl | 1 µl | 1 µl |
| of stock | 5U | 5U | 5U | 5U |
| $H_2O$ | 1.9 µl | 1.9 µl | 1.9 µl | 1.9 µl |

The tubes were incubated at 25° C. for 15 minutes. To optimize the yields of enzymatic extension, higher concentrations of dNTPs and longer reaction time may be required. The reaction was stopped by adding 4 µl of 50 mM EDTA to a final concentration of 11 µM. The supernatant was removed and the beads rinsed with 40 µl of TE buffer several times and resuspended in 35 µl of TE. The whole tube was counted and it was expected that there would be about 8% incorporation of the label added.

As a test of the synthesized oligo transfer, magnetic beads were suspended in 50 µl of 0.1M NaOH and incubated at room temperature for 10 minutes. The supernatant from each tube was removed and transfer to fresh tube. Beads were incubated a second time with 50 µl of 0.1M NaOH. As many counts seemed to remain, the first set of beads were heated to 68° C. in 50 µl NaOH which leached out a lot more counts. Each base was neutralized with 1M HCl followed by 50 µl of TE. Fresh Dynabeads were added to the melted strand and incubated at room temp for 15 minutes with gentle shaking. Supernatants were removed and saved for counting. The beads were washed several times with TE. Results are shown in Table 8.

TABLE 8

| Incorporation of label (MPROBEC 5'-CATGG—) | |
|---|---|
| A | 28,711/779,480 |
| C | 35,193/574,760 |
| G | 15,335/754,400 |
| T | 43,048/799,440 |

| | Transferred | Non bound | Unmelted | Efficiency |
|---|---|---|---|---|
| A | 9,812 | 2,330 | 10,419 | 43.4% |
| C | 13,158 | 3,950 | 8,494 | 51.4% |
| G | 5,621 | 2,672 | 1,924 | 55.0% |
| T | 15,898 | 5,287 | 5,942 | 58.6% |

Transferred refers to synthesized strand captured on fresh beads. Unbound refers to the synthesized strand that was not captured by the bead and unmelted refers to counts remaining on the original beads. As can be observed, between about 43% and 58% of the newly synthesized strands were successfully transferred indicating that an array of such strands could be successfully replicated.

Example 18

A procedure for making complex arrays by PCR. A slightly complex, but considerably improved scheme to test the generality of the new approach to SBH, without the need to synthesize, seprately, all 1024 five-mer probes has been developed. This procedure allows one to generate arrays with 5'- and/or 3'-overhangs and uses PCR to prepare the final probes used for hybridization which may easily be labeled with biotin. It also builds in a way of learning part or even all of the identity of each probe sequence.

Chemical synthesis was used to make the following sequences:

(a) 5'-GTCGACAGTT<u>GACGCTA<u>CC</u>A</u>YNNNNR<u>TGG</u>TCTAGAGCTAGC-3' (SEQ ID NO 15)

(b) 5'-CTCGAGAGTT<u>GACGCTA<u>CC</u>A</u>RNNNNY<u>TGG</u>TCTAGACCCGGG-3' (SEQ ID NO 16)

Next, enzymatic extension of the apropriate primers using a DNA polymerase in the presence of high concentrations of dNTPs was used to make the complementary duplexes. In the above sequences, N represents an equimolar mixture of all 4 bases; R is an equimolar mixture of A and G; and Y is an equimolar mixture of T and C. The underlined sequences are Bst XI and Hga I recognition sites.

| -continued | | |
|---|---|---|
| 5'-CTCGAG-3' | Xho I | 5'-C    TCGAG-3' |
| 3'-GAGCTC-5' | → | 3'-GAGCT    C-5' |
| 5'-CCCGGG-3' | Xma I | 5'-C    CCGGG-3' |
| 3'-GGGCCC-5' | → | 3'-GGGCC    C-5' |

Those cloning sites are chosen such that, even with the degeneracy allowed by the sequences 5'-YNNNNR-3' and 5'-RNNNNY-3', these enzymes will not cleave the probe regions. For cloning, duplexes (a) were cleaved with both Sal I and Nhe I restriction enzymes (or duplexes (b) with Xho I and Xma I. The resulting digestion products were directionally cloned into an appropriate vector (e.g., plasmid, phage, etc.), suitable cells were transformed with the vector, and colonies plated. Individual clones were picked and their DNA amplified by PCR using vector (a)  5'-GTCGACAGTT<u>GACGCT</u>A<u>CC</u>AYNNNNR<u>TGG</u>TCTAGAGCTAGC-3' (SEQ ID NO 15)
                                                    3'-AGATCTCGATCG-5' (SEQ ID NO 17)
                                                                    primer

(a)  5'-GTCGACAGTT<u>GACGCT</u>A<u>CC</u>AYNNNNR<u>TGG</u>TCTAGAGCTAGC-3' (SEQ ID NO 15)
     3'-CAGCTGTCAA<u>CTGCGAT<u>GGT</u></u>RNNNNY<u>ACC</u>AGATCTCGATCG-5' (SEQ ID NO 18)

(b)  5'-CTCGAGAGTT<u>GACGCT</u>A<u>CC</u>ARNNNNY<u>TGG</u>TCTAGACCCGGG-3' (SEQ ID NO 16)
                                                    3'-AGATCTGGGCCC-5' (SEQ ID NO 19)
                                                                    primer

(b)  5'-CTCGAGAGTT<u>GACGCT</u>A<u>CC</u>ARNNNNY<u>TGG</u>TCTAGACCCGGG-3' (SEQ ID NO 16)
     3'-GAGCTCTCAA<u>CTGCGAT<u>GGT</u></u>YNNNNR<u>ACC</u>AGATCTGGGCCC-5' (SEQ ID NO 20)

The seqences were designed with these internal Bst XI-cutting site which allows for the generation of complementary, 4 base 3'-overhanging single-strands which can be coverted to 5 base 3'-overhangs (see below) used for the type of positional SBH shown in FIG. 2A.

sequences downstream and upstream from the cloned sequences as the primers. This was done to increase the length of the PCR products to ease the manipulation of these products. The probe regions from individual clones were amplified by PCR with one biotinylated primer correspond-

| (SEQ ID NO 21) | 5'-CCANNNNNNTGG-3' | BstX I | 5'-CCANNNNN    NTGG-3' |
| (SEQ ID NO 22) | 3'-GGTNNNNNNACC-5' | →→→ | 3'-GGTN    NNNNNACC-5' |

The Hga I-cutting site overlaps with the Bst XI-cutting site and allows for the generation of 5 base 5'-overhanging single-strands. This is the structure needed for the type of postional SBH shown in FIG. 2B, and can also be used for subsequent sequencing of the overhangs by primer extension.

ing to the 5'-bases of the bottom strand. In a separate PCR, the lcoations of the biotins were reversed. The resulting PCR products in each case were cleaved with Bst XI, and the biotin-labeled products captured on streptavindin beads or surfaces. Note that by using PCR amplification instead of

| (SEQ ID NO 23) | 5'-GACGCNNNNNNNNNN-3' | HgaI | 5'-GACGCNNNNNNNNNN-3' |
| (SEQ ID NO 24) | 3'-CTGCGNNNNNNNNNN-5' | →→→ | 3'-CTGCGNNNNNNNNN-5' |

The 5'- and 3'-terminal sequences of strand (a) are also recognition sites for Sal I and Nhe I, respectively; the corresponding sequence in strand (b) are recognition sites for Xho I and Xma I, respectively:

| 5'-GTCGAC-3' | Sal I | 5'-G    TCGAC-3' |
| 3'-CAGCTG-5' | → | 3'-CAGCT    G-5' |
| 5'-GCTAGC-3' | Nhe I | 5'-G    CTAGC-3' |
| 3'-CGATCG-5' | → | 3'-CGATC    G-5' |

DNA purification, the need to separately purify and biotinylate each clone is also eliminated.

In parallel, all the PCR products were cleaved by Hga I which generates 5'-overhangs consisting of randomized sequences. The identity of each clone can then be determined by separate primer extensions of each of the two DNA pieces resulting from Hga I cleavage. For each pair of sequences, which derive from the same clone, the overhangs must be complementary. Therefore, sequencing just three bases on each fragment strand will given the entire structure of two probes. This plus/minus sequencing can be done in microtire plates and is easily automated. It will fail only in the few cases were 5'-RNNNNY-3' in strand (b) contains 5'-GACGC-3', which is the recognition site for Hga I. The number of prier extension reactions required can be reduced by synthesis of more restricted pools of sequences. For example, using 4 pools where the base in one particular postion is known in advance, such as 5'-YNNANR-3'.

To make the probes needed for positional SBH (as sown in FIG. 2A), the duplex PCR products are first attached to a solid support through streptavidin. They are then cleaved with Bst XI to generate the following pairs of products:

5'-B-GTCGACAGTTGACGCTACCAYNNNN-3' (SEQ ID NO 25)

3'-CAGCTGTCAACTGCGATGGTR-5' (SEQ ID NO 26)

5'-B-GCTAGCTCTAGACCAYNNNN-3' (SEQ ID NO 27)

3'-CGATCGAGATCTGGTR-5' (SEQ ID NO 28)

5'-B-CTCGAGAGTTGACGCTACCARNNNN-3' (SEQ ID NO 29)

3'-GAGCTCTCAACTGCGATGGTY-5' (SEQ ID NO 30)

5'-B-CCCGGGTCTAGACCARNNNN-3' (SEQ ID NO 31)

3'-GGGCCCAGATCTGGTY-5' (SEQ ID NO 32)

The 5 base 3' overhangs needed for positional SBH are made by replacing the complementary (non-biotinylated) strands with constant strands which are one base shorter.

5'-B-GTCGACAGTTGACGCTACCAYNNNN-3' (SEQ ID NO 25)

3'-CAGCTGTCAACTGCGATGGT-5' (SEQ ID NO 33)

5'-B-GCTAGCTCTAGACCAYNNNN-3' (SEQ ID NO 27)

3'-CGATCGAGATCTGGT-5' (SEQ ID NO 34)

5'-B-CTCGAGAGTTGACGCTACCARNNNN-3' (SEQ ID NO 29)

3'-GAGCTCTCAACTGCGATGGT-5' (SEQ ID NO 35)

5'-B-CCCGGGTCTAGACCARNNNN-3' (SEQ ID NO 31)

3'-GGGCCCAGATCTGGT-5' (SEQ ID NO 36)

This generates the 5 base 3'-overhanging arrays amenable to extension with Sequenase version 2.0 after the ligation step shown in FIGS. 2A and B. Randomly chosen arrays of 5,120 (5× coverage) are needed to ensure that all of the sequences (>99%) are present, but this array is much larger than optimal. In practice, a library will need only provide approximately 63% of the sequences and, if necessary, can be supplemented to fill in the missing variable clones by direct synthesis.

Other embodiments and uses of the invention will be apparent to those skilled in the art from consideration of the specification and practice of the invention disclosed herein. It is intended that the specification and examples be considered exemplary only, with the true scope and spirit of the invention being indicated by the following claims.

We claim:

1. A method for replicating an array of single-stranded probes on a solid support comprising the steps of:
    a) synthesizing an array of nucleic acids each comprising a non-variant sequence of length C at a 3'-terminus and a variable sequence of length R at a 5'-terminus;
    b) fixing the array to a first solid support;
    c) synthesizing a set of nucleic acids each comprising a sequence complementary to the non-variant sequence;
    d) hybridizing the nucleic acids of the set to the array;
    e) enzymatically extending the nucleic acids of the set using the variable sequences of the array as templates;
    f) denaturing the set of extended nucleic acids; and
    g) fixing the denatured nucleic acids of the set to a second solid support to create the replicated array of single-stranded probes.

2. The method of claim 1 wherein the nucleic acids of the set are conjugated with biotin and the second solid support comprises streptavidin.

3. The method of claim 1 wherein the nucleic acids of the array are between about 15–30 nucleotides in length and the nucleic acids of the set are between about 10–25 nucleotides in length.

4. The method of claim 1 wherein C is between about 7–20 nucleotides and R is between about 3–5 nucleotides.

5. The method of claim 1 wherein the solid supports are selected from the group consisting of plastics, ceramics, metals, resins, gels, membranes and chips.

6. The method of claim 1 wherein the nucleic acids of the set are enzymatically extended with a DNA polymerase and one or more deoxynucleotide triphosphates.

7. The method of claim 1 wherein denaturing is performed with heat, alkali, organic solvents, binding proteins, enzymes, salts or combinations thereof.

8. The method of claim 1 further comprising the step of hybridizing the replicated array with a second set of nucleic acids complementary to the non-variant sequence of the replicated array to create a double-stranded replicated array.

9. The method of claim 1 wherein the solid supports are two-dimensional or three-dimensional matrixes.

10. The method of claim 8 wherein a double-stranded portion of the partially double-stranded replicated array comprise a restriction endonuclease site.

11. The method of claim 8 wherein the partially double-stranded replicated array have 5'- or 3'-overhangs.

12. The method of claim 8 wherein the partially double-stranded replicated array comprises about $4^R$ different probes.

13. The method of claim 8 wherein the partially double-stranded replicated array comprise a detectable label.

14. The method of claim 13 wherein the detectable label is selected from the group consisting of radioisotopes, stable isotopes, enzymes, fluorescent and luminescent chemicals, chromatic chemicals, metals, electric charges, and spatial chemicals.

15. A method for replicating an array of single-stranded probes on a solid support comprising the steps of:
    a) fixing a first array of nucleic acids each comprising a non-variant sequence of length C at a 3'-terminus and a variable sequence of length R at a 5'-terminus to a first solid support;
    b) synthesizing a first set of nucleic acids each comprising a sequence complementary to the non-variant sequence;
    c) hybridizing the nucleic acids of the first set to the first array;
    d) enzymatically extending the nucleic acids of the first set using the variable sequences of the first array as templates;
    e) denaturing the first set of extended nucleic acids;
    f) fixing the denatured nucleic acids of the first set to a second solid support to create the replicated array of single-stranded probes; and
    g) hybridizing the replicated array with a second set of nucleic acids complementary to the constant sequence of the replicated array to create a partially double-stranded replicated array.

16. The method of claim 15 wherein the nucleic acids of the first set are conjugated with biotin and the second solid support comprises streptavidin.

17. The method of claim 15 wherein the nucleic acids of the first array are between about 15–30 nucleotides in length and the nucleic acids of the first set are between about 10–25 nucleotides in length.

18. The method of claim 15 wherein C is between about 7–20 nucleotides and R is between about 3–5 nucleotides.

19. The method of claim 15 wherein the partially double-stranded replicated array comprises about $4^R$ different probes.

20. The method of claim 15 wherein the solid supports are selected from the group consisting of plastics, ceramics, metals, resins, gels, membranes and chips.

21. The method of claim 15 wherein the solid supports are two-dimensional or three-dimensional matrixes.

22. A method for replicating an array of single-stranded probes on a solid support comprising the steps of:
   a) fixing an array of nucleic acids each comprising a non-variant sequence of length C at a 3'-terminus and a variable sequence of length R at a 5'-terminus to a first solid support;
   b) synthesizing a set of nucleic acids each comprising a sequence complementary to the non-variant sequence;
   c) hybridizing the nucleic acids of the set to the array;
   d) enzymatically extending the nucleic acids of the set using the variable sequences of the array as templates;
   e) denaturing the set of extended nucleic acids; and
   f) fixing the denatured nucleic acids of the set to a second solid support with a streptavidin-biotin or an avidin-biotin bond to create the replicated array of single-stranded probes.

23. The method of claim 22 wherein the nucleic acids of the array are between about 15–30 nucleotides in length and the nucleic acids of the set are between about 10–25 nucleotides in length.

24. The method of claim 22 wherein C is between about 7–20 nucleotides and R is between about 3–5 nucleotides.

25. The method of claim 22 wherein the solid supports are selected from the group consisting of plastics, ceramics, metals, resins, gels, membranes and chips.

26. The method of claim 22 wherein the nucleic acids of the set are enzymatically extended with a DNA polymerase and one or more deoxynucleotide triphosphates.

27. The method of claim 22 wherein denaturing is performed with heat, alkali, organic solvents, binding proteins, enzymes, salts or combinations thereof.

28. The method of claim 22 wherein the solid supports are two-dimensional or three-dimensional matrixes.

29. The method of claim 22 wherein the replicated array comprises about $4^R$ different probes.

* * * * *

UNITED STATES PATENT AND TRADEMARK OFFICE
CERTIFICATE OF CORRECTION

PATENT NO.   : 5,795,714
DATED        : 08/18/98
INVENTOR(S)  : Charles R. Cantor et al.

It is certified that error appears in the above-indentified patent and that said Letters Patent is hereby corrected as shown below:

Col. 1, Line 4:   Please insert --This invention was made with Government support under grant number DE-FG02-93-ER61609 awarded by the Department of Energy. The United States Government may have certain rights in this invention.--

Signed and Sealed this

First Day of June, 1999

Attest:

Q. TODD DICKINSON

Attesting Officer          Acting Commissioner of Patents and Trademarks